United States Patent
Gonzales et al.

(10) Patent No.: US 12,319,694 B2
(45) Date of Patent: Jun. 3, 2025

(54) HETEROCYCLIC NITROGEN-CONTAINING PURINE DERIVATIVES, PHARMACEUTICAL PREPARATIONS CONTAINING THESE DERIVATIVES AND THEIR USE IN NEUROPROTECTION

(71) Applicants: UNIVERZITA PALACKEHO, Olomouc (CZ); FAKULTNI NEMOCNICE OLOMOUC, Olomouc (CZ)

(72) Inventors: Gabriel Gonzales, Vrbatky (CZ); Vaclav Mik, Grygov (CZ); Noemi Bucharova, Vysokov (CZ); Jiri Gruz, Bohunovice (CZ); Petr Kanovsky, Vranov (CZ); Miroslav Strnad, Olomouc (CZ); Marek Zatloukal, Sumperk (CZ)

(73) Assignees: UNIVERZITA PALACKEHO, Olomouc (CZ); FAKULTNI NEMOCNICE OLOMOUC, Olomouc (CZ)

( * ) Notice: Subject to any disclaimer, the term of this patent is extended or adjusted under 35 U.S.C. 154(b) by 933 days.

(21) Appl. No.: 17/426,804

(22) PCT Filed: Jan. 27, 2020

(86) PCT No.: PCT/CZ2020/050004
§ 371 (c)(1),
(2) Date: Jul. 29, 2021

(87) PCT Pub. No.: WO2020/164648
PCT Pub. Date: Aug. 20, 2020

(65) Prior Publication Data
US 2022/0127269 A1 Apr. 28, 2022

(30) Foreign Application Priority Data
Feb. 12, 2019 (CZ) .................. CZ2019-82

(51) Int. Cl.
C07D 473/16 (2006.01)
A61K 31/52 (2006.01)
A61P 25/16 (2006.01)
A61P 25/28 (2006.01)

(52) U.S. Cl.
CPC ............ *C07D 473/16* (2013.01); *A61K 31/52* (2013.01); *A61P 25/16* (2018.01); *A61P 25/28* (2018.01)

(58) Field of Classification Search
None
See application file for complete search history.

(56) References Cited

FOREIGN PATENT DOCUMENTS

| WO | 2015113451 A1 | 8/2015 |
| WO | 2015113452 A1 | 8/2015 |

OTHER PUBLICATIONS

Fiorini et. al. ((1998), Solution-Phase Synthesis of 2,6,9-Trisubstituted Purine, Tetrahedron Letters, 39, 1827-1830 (Year: 1998).*
Fiorini MT et al: "Solution-Phase Synthesis of 2,6,9-Trisubstituted Purines", Tetrahedron Letters, Elsevier Ltd, Amsterdam, NL, vol. 39, No. 13, Mar. 26, 1998 (Mar. 26, 1998), pp. 1827-1830, XP004108488, ISSN: 0040-4039, retrieved Jul. 28, 2021.
Huang H et al: Discovery of novel purine derivatives with potent and selective inhibitory activity against c-Src tyrosine kinase, Bioorganic & Medicinal Chemistry : A Tetrahedron Publication for the Rapid Dissemination of Full Original Research Papers and Critical Reviews on Biomolecular Chemistry, Medicinal Chemistry and Related Disciplines, Elsevier, NL, vol. 18, No. 13, Jul. 1, 2010 (Jul. 1, 2010), pp. 4615-4624, XP027083649, ISSN: 0968-0896, retrieved Jul. 28, 2021.
International Search Report and Written Opinion for corresponding PCT application No. PCT/CZ2020/050004, mailed Mar. 30, 2020.

* cited by examiner

*Primary Examiner* — Juliet C Switzer
*Assistant Examiner* — Dawanna Shar-Day White
(74) *Attorney, Agent, or Firm* — Notaro, Michalos & Zaccaria P.C.

(57) ABSTRACT

Heterocyclic nitrogen-containing purine derivatives and their use in the medicinal applications and compositions containing these derivatives is disclosed. A new generation of compounds possessing selective antineurodegenerative properties on neuronal cells and tissues and that can be particularly used in the treatment and prophylaxis of neurodegenerative disease, particularly in the treatment and prophylaxis of Parkinson's disease is also disclosed.

9 Claims, 1 Drawing Sheet

HETEROCYCLIC NITROGEN-CONTAINING PURINE DERIVATIVES, PHARMACEUTICAL PREPARATIONS CONTAINING THESE DERIVATIVES AND THEIR USE IN NEUROPROTECTION

FIELD OF ART

The invention relates to heterocyclic nitrogen-containing purine derivatives, to their use in neuroprotection, and in particular for the treatment of Parkinson's disease and pharmaceutical compositions containing these derivatives.

BACKGROUND ART

The incidence of neurodegenerative diseases experiences a dramatic rise. In particular, Alzheimer's disease (AD) doubles in frequency in population over 65 years of age. Moreover, AD affects up to 50% of population over the age of 85 (Qiu, Kivipelto and von Strauss et al., Dial Clin Neurosci, 2009, 11, 111).

Similarly, Parkinson's disease (PD), amyotrophic lateral sclerosis (ALS), progressive supranuclear palsy (PSP), corticobasal degeneration (CBD), frontotemporal dementia (FTD), Lewy body dementia (DLB), Huntington's disease (HD), multiple system atrophy (MSA), chronic traumatic encephalopathy (CTE), spinocerebellar ataxias are also linked with aging of population. Neurodegenerative diseases are currently a burning issue of the modern society, due to the cost of treatment and lack of efficient medication (Christophe Coupé et al., Eur Neurol Rev, 2013, 8, 38; Levy et al., Arch Neurol, 2007, 64, 1242; Shah et al., Lancet Neurol, 2016, 15, 1285). Neurodegenerative diseases are tightly linked with several pathological events such as progressive loss of function of neurons leading to their death by apoptosis, impaired autophagy, protein aggregation, inflammation, oxidative stress, mitochondrial dysfunction and excitotoxicity (Jeffrey, L. C.; Jagan, A. P.; (2016). Neurodegenerative Diseases Evolving Unifying Principles In *Neurodegenerative Diseases Unifying Principles* (pp. 1-14). Oxford, UK).

Currently, trends of neurodegenerative diseases therapy are focused toward the disease modifying therapy that targets pathological mechanisms of disease, which lead to progression and neuronal death. Current therapeutical strategies involve 1) direct effects on neurons via reduction of oxidative stress and induction of Nrf-2 pathway, enhancement of mitochondrial vitality, decreasing of apoptosis (induction of Akt pathways, Bcl-2 up-regulation), protection of axons and their functions and production of trophic factors; or 2) indirect effects by regulation of cells responsible for inflammatory processes such as microglia and astrocytes. A final result disease modifying therapy is the achievement of neuroprotection (Cummings et al., Transl Neurodeg, 2017, 6, 25).

It is therefore an object of the present invention to provide a new generation of purine derivatives which exhibit potent and selective anti-neurodegenerative properties on neuronal cells and tissues and can be advantageously used in the treatment and prophylaxis of neurodegenerative diseases, preferably Parkinson's disease.

DISCLOSURE OF THE INVENTION

The object of this invention are heterocyclic nitrogen-containing purine derivatives of the general formula I,

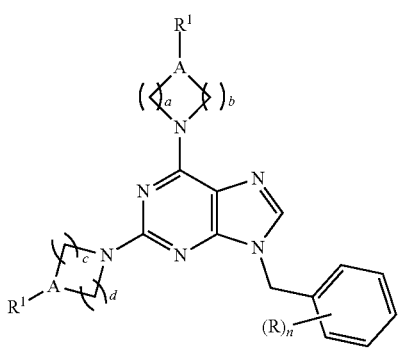

wherein,
R are independently selected from the group consisting of H, F, Cl, Br, methyl, OH, and methoxy, and n=1 or 2;
$R^1$ is independently on each occurrence H or methyl, or R1 is not present;
A is independently on each occurrence selected from the group consisting of C, N, O, S;
a, b, c, d are, independently of each other, an integer selected from 1, 2, 3;
provided that the compound of formula I is not 2,6-dimorpholino-9-benzylpurine;
and the pharmaceutically acceptable salts thereof, in particular salts with alkali metals, ammonium or amines, or addition salts with acids.

The person skilled in the art will understand that the substituent $R^1$ is H or methyl when A is C or N with at least one free valence. The substituent $R^1$ is not present when A is O or S.

In some embodiments, the compounds of the general formula I bear a substituent in position 2, i.e., the ring —[N—$(CH_2)_c$-A($R^1$)—$(CH_2)_d$—], which is selected from the group consisting of azetidin-1-yl, pyrrolidin-1-yl, piperidin-1-yl, morpholino, thiomorpholino, piperazin-1-yl, 4-methylpiperazin-1-yl, azepan-1-yl, azocan-1-yl, 1,5-oxazocan-5-yl, and 1,5-thiazocan-5-yl.

In some embodiments, the compounds of the general formula I bear a substituent in position 6, i.e., the ring —[N—$(CH_2)_a$-A($R^1$)—$(CH_2)_b$—], which is selected from the group consisting of azetidin-1-yl, pyrrolidin-1-yl, piperidin-1-yl, morpholino, thiomorpholino, piperazin-1-yl, 4-methylpiperazin-1-yl, azepan-1-yl, azocan-1-yl, 1,5-oxazocan-5-yl, and 1,5-thiazocan-1-yl.

In some embodiments, the compounds of the general formula I bear a substituent in position 9, i.e., the substituent —$CH_2$—$C_6H_4(R)_n$, which is selected from the group consisting of benzyl, 2-fluorobenzyl, 3-fluorobenzyl, 4-fluorobenzyl, 2-chlorobenzyl, 3-chlorobenzyl, 4-chlorobenzyl, 2,6-dichlorobenzyl, 2-bromobenzyl, 3-bromobenzyl, 4-bromobenzyl, 2-methylbenzyl, 3-methylbenzyl, 4-methylbenzyl, 2-hydroxybenzyl, 3-hydroxybenzyl, 4-hydroxybenzyl, 2-methoxybenzyl, 3-methoxybenzyl, 4-methoxybenzyl.

Individual compounds as shown in the examples represent individual preferred embodiments of the present invention. Preferred compounds of the invention are the following compounds of the general formula I:

2-(azetidin-1-yl, pyrrolidin-1-yl, piperidin-1-yl, morfolino, thiomorfolino, piperazin-1-yl, 4-methylpiperazin-1-yl, azepan-1-yl, azocan-1-yl, 1,5-oxazocan-5-yl, 1,5-thiazocan-5-yl)-6-(azetidin-1-yl)-9-(benzyl, 2-fluorobenzyl, 3-fluorobenzyl, 4-fluorobenzyl, 2-chlorobenzyl, 3-chlorobenzyl, 4-chlorobenzyl, 2,6-dichlorobenzyl, 2-bromobenzyl, 3-bromobenzyl, 4-bromobenzyl, 2-methylbenzyl, 3-methylbenzyl, 4-methylbenzyl, 2-hydroxybenzyl, 3-hydroxybenzyl, 4-hydroxybenzyl, 2-methoxybenzyl, 3-methoxybenzyl, 4-methoxybenzyl)-9H-purine; 2-(azetidin-1-yl, pyrrolidin-1-yl, piperidin-1-yl, morfolino, thiomorfolino, piperazin-1-yl, 4-methylpiperazin-1-yl, azepan-1-yl, azocan-1-yl, 1,5-oxazocan-5-yl, 1,5-thiazocan-5-yl)-6-(pyrrolidin-1-yl)-9-(benzyl, 2-fluorobenzyl, 3-fluorobenzyl, 4-fluorobenzyl, 2-chlorobenzyl, 3-chlorobenzyl, 4-chlorobenzyl, 2,6-dichlorobenzyl, 2-bromobenzyl, 3-bromobenzyl, 4-bromobenzyl, 2-methylbenzyl, 3-methylbenzyl, 4-methylbenzyl, 2-hydroxybenzyl, 3-hydroxybenzyl, 4-hydroxybenzyl, 2-methoxybenzyl, 3-methoxybenzyl, 4-methoxybenzyl)-9H-purine; 2-(azetidin-1-yl, pyrrolidin-1-yl, piperidin-1-yl, morfolino, thiomorpholino, piperazin-1-yl, 4-methylpiperazin-1-yl, azepan-1-yl, azocan-1-yl, 1,5-oxazocan-5-yl, 1,5-thiazocan-5-yl)-6-(piperidin-1-yl)-9-(benzyl, 2-fluorobenzyl, 3-fluorobenzyl, 4-fluorobenzyl, 2-chlorobenzyl, 3-chlorobenzyl, 4-chlorobenzyl, 2,6-dichlorobenzyl, 2-bromobenzyl, 3-bromobenzyl, 4-bromobenzyl, 2-methylbenzyl, 3-methylbenzyl, 4-methylbenzyl, 2-hydroxybenzyl, 3-hydroxybenzyl, 4-hydroxybenzyl, 2-methoxybenzyl, 3-methoxybenzyl, 4-methoxybenzyl)-9H-purine; 2-(azetidin-1-yl, pyrrolidin-1-yl, piperidin-1-yl, morfolino, thiomorfolino, piperazin-1-yl, 4-methylpiperazin-1-yl, azepan-1-yl, azocan-1-yl, 1,5-oxazocan-5-yl, 1,5-thiazocan-5-yl)-6-morfolino-9-(benzyl, 2-fluorobenzyl, 3-fluorobenzyl, 4-fluorobenzyl, 2-chlorobenzyl, 3-chlorobenzyl, 4-chlorobenzyl, 2,6-dichlorobenzyl, 2-bromobenzyl, 3-bromobenzyl, 4-bromobenzyl, 2-methylbenzyl, 3-methylbenzyl, 4-methylbenzyl, 2-hydroxybenzyl, 3-hydroxybenzyl, 4-hydroxybenzyl, 2-methoxybenzyl, 3-methoxybenzyl, 4-methoxybenzyl)-9H-purine; 2-(azetidin-1-yl, pyrrolidin-1-yl, piperidin-1-yl, morfolino, thiomorfolino, piperazin-1-yl, 4-methylpiperazin-1-yl, azepan-1-yl, azocan-1-yl, 1,5-oxazocan-5-yl, 1,5-thiazocan-5-yl)-6-thiomorfolino-9-(benzyl, 2-fluorobenzyl, 3-fluorobenzyl, 4-fluorobenzyl, 2-chlorobenzyl, 3-chlorobenzyl, 4-chlorobenzyl, 2,6-dichlorobenzyl, 2-bromobenzyl, 3-bromobenzyl, 4-bromobenzyl, 2-methylbenzyl, 3-methylbenzyl, 4-methylbenzyl, 2-hydroxybenzyl, 3-hydroxybenzyl, 4-hydroxybenzyl, 2-methoxybenzyl, 3-methoxybenzyl, 4-methoxybenzyl)-9H-purine; 2-(azetidin-1-yl, pyrrolidin-1-yl, piperidin-1-yl, morfolino, thiomorfolino, piperazin-1-yl, 4-methylpiperazin-1-yl, azepan-1-yl, azocan-1-yl, 1,5-oxazocan-5-yl, 1,5-thiazocan-5-yl)-6-(piperazin-1-yl)-9-(benzyl, 2-fluorobenzyl, 3-fluorobenzyl, 4-fluorobenzyl, 2-chlorobenzyl, 3-chlorobenzyl, 4-chlorobenzyl, 2,6-dichlorobenzyl, 2-bromobenzyl, 3-bromobenzyl, 4-bromobenzyl, 2-methylbenzyl, 3-methylbenzyl, 4-methylbenzyl, 2-hydroxybenzyl, 3-hydroxybenzyl, 4-hydroxybenzyl, 2-methoxybenzyl, 3-methoxybenzyl, 4-methoxybenzyl)-9H-purine; 2-(azetidin-1-yl, pyrrolidin-1-yl, piperidin-1-yl, morfolino, thiomorfolino, piperazin-1-yl, 4-methylpiperazin-1-yl, azepan-1-yl, azocan-1-yl, 1,5-oxazocan-5-yl, 1,5-thiazocan-5-yl)-6-(4-methylpiperazin-1-yl)-9-(benzyl, 2-fluorobenzyl, 3-fluorobenzyl, 4-fluorobenzyl, 2-chlorobenzyl, 3-chlorobenzyl, 4-chlorobenzyl, 2,6-dichlorobenzyl, 2-bromobenzyl, 3-bromobenzyl, 4-bromobenzyl, 2-methylbenzyl, 3-methylbenzyl, 4-methylbenzyl, 2-hydroxybenzyl, 3-hydroxybenzyl, 4-hydroxybenzyl, 2-methoxybenzyl, 3-methoxybenzyl, 4-methoxybenzyl)-9H-purine; 2-(azetidin-1-yl, pyrrolidin-1-yl, piperidin-1-yl, morfolino, thiomorfolino, piperazin-1-yl, 4-methylpiperazin-1-yl, azepan-1-yl, azocan-1-yl, 1,5-oxazocan-5-yl, 1,5-thiazocan-5-yl)-6-(azepan-1-yl)-9-(benzyl, 2-fluorobenzyl, 3-fluorobenzyl, 4-fluorobenzyl, 2-chlorobenzyl, 3-chlorobenzyl, 4-chlorobenzyl, 2,6-dichlorobenzyl, 2-bromobenzyl, 3-bromobenzyl, 4-bromobenzyl, 2-methylbenzyl, 3-methylbenzyl, 4-methylbenzyl, 2-hydroxybenzyl, 3-hydroxybenzyl, 4-hydroxybenzyl, 2-methoxybenzyl, 3-methoxybenzyl, 4-methoxybenzyl)-9H-purine; 2-(azetidin-1-yl, pyrrolidin-1-yl, piperidin-1-yl, morfolino, thiomorfolino, piperazin-1-yl, 4-methylpiperazin-1-yl, azepan-1-yl, azocan-1-yl, 1,5-oxazocan-5-yl, 1,5-thiazocan-5-yl)-6-(azocan-1-yl)-9-(benzyl, 2-fluorobenzyl, 3-fluorobenzyl, 4-fluorobenzyl, 2-chlorobenzyl, 3-chlorobenzyl, 4-chlorobenzyl, 2,6-dichlorobenzyl, 2-bromobenzyl, 3-bromobenzyl, 4-bromobenzyl, 2-methylbenzyl, 3-methylbenzyl, 4-methylbenzyl, 2-hydroxybenzyl, 3-hydroxybenzyl, 4-hydroxybenzyl, 2-methoxybenzyl, 3-methoxybenzyl, 4-methoxybenzyl)-9H-purine; 2-(azetidin-1-yl, pyrrolidin-1-yl, piperidin-1-yl, morfolino, thiomorfolino, piperazin-1-yl, 4-methylpiperazin-1-yl, azepan-1-yl, azocan-1-yl, 1,5-oxazocan-5-yl, 1,5-thiazocan-5-yl)-6-(1,5-oxazocan-5-yl)-9-(benzyl, 2-fluorobenzyl, 3-fluorobenzyl, 4-fluorobenzyl, 2-chlorobenzyl, 3-chlorobenzyl, 4-chlorobenzyl, 2,6-dichlorobenzyl, 2-bromobenzyl, 3-bromobenzyl, 4-bromobenzyl, 2-methylbenzyl, 3-methylbenzyl, 4-methylbenzyl, 2-hydroxybenzyl, 3-hydroxybenzyl, 4-hydroxybenzyl, 2-methoxybenzyl, 3-methoxybenzyl, 4-methoxybenzyl)-9H-purine; 2-(azetidin-1-yl, pyrrolidin-1-yl, piperidin-1-yl, morfolino, thiomorfolino, piperazin-1-yl, 4-methylpiperazin-1-yl, azepan-1-yl, azocan-1-yl, 1,5-oxazocan-5-yl, 1,5-thiazocan-5-yl)-6-(1,5-thiazocan-1-yl)-9-(benzyl, 2-fluorobenzyl, 3-fluorobenzyl, 4-fluorobenzyl, 2-chlorobenzyl, 3-chlorobenzyl, 4-chlorobenzyl, 2,6-dichlorobenzyl, 2-bromobenzyl, 3-bromobenzyl, 4-bromobenzyl, 2-methylbenzyl, 3-methylbenzyl, 4-methylbenzyl, 2-hydroxybenzyl, 3-hydroxybenzyl, 4-hydroxybenzyl, 2-methoxybenzyl, 3-methoxybenzyl, 4-methoxybenzyl)-9H-purine.

Generally, the most preferred compounds of the general formula I are:
2,6-di(azetidin-1-yl)-9-(3-hydroxybenzyl)-9H-purine,
2,6-di(azetidin-1-yl)-9-(4-hydroxybenzyl)-9H-purine,
9-(4-hydroxybenzyl)-2,6-di(pyrrolidin-1-yl)-9H-purine, 9-benzyl-2-(piperidin-1-yl)-6-(pyrrolidin-1-yl)-9H-purine, 9-benzyl-6-(piperidin-1-yl)-2-(pyrrolidin-1-yl)-9H-purine, 9-benzyl-2,6-dithiomorpholino-9H-purine, 9-(4-hydroxybenzyl)-2,6-dithiomorpholino-9H-purine, 2-(azetidin-1-yl)-9-(4-hydroxybenzyl)-6-thiomorpholino-9H-purine, 9-(4-hydroxybenzyl)-2-(pyrrolidin-1-yl)-6-thiomorpholino-9H-purine, 2,6-di(azepan-1-yl)-9-(4-hydroxybenzyl)-9H-purine.

The compounds of the present invention have a wide range of biological activities, including activities in increasing viability of neuronal cells, reducing oxidative stress, neuroprotectivity and Nrf-2 activation, which are especially useful in pharmaceutical applications to treat neurodegenerative diseases and correspond to the spectrum of effects required of the agents intended for such treatment.

This invention also provides the compounds of the general formula I for use in activation of the Nrf2-antioxidant response element signaling pathway, which controls the expression of genes whose protein products are involved in the detoxification and elimination of reactive oxidants and electrophilic agents through conjugative reactions and by enhancing cellular antioxidant capacity.

This invention also provides the compounds of the general formula I for use as antioxidants for inhibiting adverse metabolic processes in mammals and plants either in vivo or in vitro.

The present invention also provides the compounds of the general formula I for use as medicaments.

The invention preferably relates to the compounds of the general formula I for use in the treatment or prophylaxis of neurodegenerative diseases, in particular selected from amyotrophic lateral sclerosis, Parkinson's disease, Alzheimer's disease, Huntington's disease, progressive supranuclear palsy, corticobasal degeneration, frontotemporal dementia, Lewy body dementia, multiple system atrophy, chronic traumatic encephalopathy, spinocerebellar ataxias.

In a preferred embodiment, the invention provides the compounds of the general formula I for use in the treatment and prophylaxis of Parkinson's disease.

The present invention further provides pharmaceutical compositions comprising one or more compounds of the general formula I together with at least one pharmaceutically acceptable carrier.

Pharmaceutical Compositions

Suitable routes for administration include oral, rectal, topical (including dermal, ocular, buccal and sublingual), vaginal and parenteral (including subcutaneous, intramuscular, intravitreous, intravenous, intradermal, intrathecal and epidural).

The therapeutic compositions generally comprise about 1% to about 95% of the active ingredient. Single-dose forms of administration preferably comprise about 20% to about 90% of the active ingredient and administration forms which are not single-dose preferably comprise about 5% to about 20% of the active ingredient. Unit dose forms are, for example, coated tablets, tablets, ampoules, vials, suppositories or capsules. Other forms of administration are, for example, ointments, creams, pastes, foams, tinctures, lipsticks, drops, sprays, dispersions and the like. Examples are capsules containing from about 0.05 g to about 1.0 g of the active ingredient.

The pharmaceutical and cosmetic compositions of the present invention are prepared in a manner known per se, for example by means of conventional mixing, granulating, coating, dissolving or lyophilizing processes.

Preferably, solutions of the active ingredient, and in addition also suspensions or dispersions, especially isotonic aqueous solutions, dispersions or suspensions, are used, it being possible for these to be prepared before use, for example in the case of lyophilized compositions which comprise the active substance by itself or together with a carrier, for example mannitol. The compositions can be sterilized and/or comprise excipients, for example preservatives, stabilizers, wetting agents and/or emulsifiers, solubilizing agents, salts for regulating the osmotic pressure and/or buffers, and they are prepared in a manner known per se, for example by means of conventional dissolving or lyophiliz-ing processes. The solutions or suspensions mentioned can comprise viscosity-increasing substances, such as sodium carboxymethylcellulose, carboxymethylcellulose, dextran, polyvinylpyrrolidone or gelatin. Suspensions in oil comprise, as the oily component, vegetable, synthetic or semi-synthetic oils customary for injection purposes. Oils which may be mentioned are, in particular, liquid fatty acid esters which contain, as the acid component, a long-chain fatty acid having 8-22, in particular 12-22, carbon atoms (e.g., lauric acid, tridecylic acid, myristic acid, pentadecylic acid, palmitic acid, margaric acid, stearic acid, acid, arachidonic acid, behenic acid, and the like) or corresponding unsaturated acids (e.g., oleic acid, elaidic acid, euric acid, brasidic acid or linoleic acid). Other additional ingredients known in the art can be included if desired (e.g., antioxidants such as vitamin E, β-carotene, or 3,5-di-tert-butyl-4-hydroxytoluene, and the like). The alcohol component of these fatty acid esters generally contains no more than about 6 carbon atoms and can be mono- or polyhydric. Mono-, di-, or trihydric alcohols such as methanol, ethanol, propanol, butanol, or pentanol, or isomers thereof, can be used; glycols and glycerols are generally preferred. Fatty acid esters can therefore include, for example, ethyl oleate, isopropyl myristate, isopropyl palmitate, "Labrafil M 2375" (polyoxyethylene glycerol trioleate from Gattefoseé, Paris), "Labrafil M 1944 CS" (unsaturated polyglycolated glycerides prepared by an alcoholysis of apricot kernel oil and made up of glycerides and polyethylene glycol esters; from Gattefoseé, Paris), "Labrasol" (saturated polyglycolated glycerides prepared by an alcoholysis of TCM and made up of glycerides and polyethylene glycol esters; from Gattefoseé, Paris), and/or "Miglyol 812" (triglyceride of saturated fatty acids of chain length C8 to C12 from Hills AG, Germany), and in particular vegetable oils, such as cottonseed oil, almond oil, olive oil, castor oil, sesame oil, soybean oil and, in particular, groundnut oil as well as mixtures thereof.

The preparation of the compositions intended for human use should, of course, be carried out in the customary and approved manner under sterile conditions, and maintained under appropriate conditions up to and including the time of use.

For example, pharmaceutical compositions for oral use can be obtained by combining the active ingredient with one or more solid carriers, if appropriate granulating the resulting mixture, and, if desired, processing the mixture or granules to tablets or coated tablet cores, if appropriate by addition of additional excipients. Suitable carriers are, in particular, fillers, such as sugars, for example lactose, sucrose, mannitol or sorbitol, cellulose preparations and/or calcium phosphates, for example tricalcium diphosphate, or calcium hydrogen phosphate, and furthermore binders, such as starches, for example maize, wheat, rice or potato starch, methylcellulose, hydroxypropylmethylcellulose, sodium carboxymethylcellulose and/or polyvinylpyrrolidone, and/or, if desired, desintegrators, such as the above mentioned starches, and furthermore carboxymethyl-starch, cross-linked polyvinylpyrrolidone, alginic acid or a salt thereof, such as sodium alginate. Additional excipients are, in particular, flow regulators and lubricants, for example salicylic acid, talc, stearic acid or salts thereof, such as magnesium stearate or calcium stearate, and/or polyethylene glycol, or derivatives thereof.

Coated tablet cores can be provided with suitable coatings which, if appropriate, are resistant to gastric juice, the coatings used being, inter alia, concentrated sugar solutions, which, if appropriate, comprise gum arabic, talc, polyvinylpyrrolidone, polyethylene glycol and/or titanium dioxide, coating solutions in suitable organic solvents or solvent mixtures or, for the preparation of coatings which are resistant to gastric juice, solutions of suitable cellulose preparations, such as acetylcellulose phthalate or hydroxypropylmethylcellulose phthalate. Dyes or pigments can be admixed to the tablets or coated tablet coatings, for example for identification or characterization of different doses of active ingredient.

Pharmaceutical compositions, which can be used orally, can also be in the form hard capsules of gelatine and soft, closed capsules of gelatine and a plasticizer, such as glycerol or sorbitol. The hard capsules can contain the active ingredient in the form of granules, mixed for example with fillers, such as maize starch, binders and/or lubricants, such as talc or magnesium stearate, and stabilizers if appropriate. In soft capsules, the active ingredient is preferably dissolved or suspended in suitable liquid excipients, such as greasy oils, paraffin oil or liquid polyethylene glycol's or fatty acid esters of ethylene glycol or propylene glycol, it being likewise possible to add stabilizers and detergents such as, for example, the polyethylene sorbitan fatty acid ester type.

Other oral forms of administration include, for example, syrups prepared in the customary manner, which comprise the active ingredient, for example, in suspended form and in a concentration of about 5% to 20%, preferably about 10% or in a similar concentration which results in a suitable individual dose, for example, when 5 or 10 mL are measured out. Other forms include pulverulent or liquid concentrates for preparing shakes, beverages, and the like. Such concentrates can also be packed in unit dose quantities.

Pharmaceutical compositions, which can be used rectally, are, for example, suppositories that comprise a combination of the active ingredient with a suppository base. Suitable suppository bases are, for example, naturally occurring or synthetic triglycerides, paraffin hydrocarbons, polyethylene glycols or higher alkanols.

Compositions which are suitable for parental administration are aqueous solutions of an active ingredient in water-soluble form, for example of water-soluble salt, or aqueous injection suspensions, which comprise viscosity-increasing substances, for example sodium carboxymethylcellulose, sorbitol and/or dextran, and if appropriate, stabilizers. The active ingredient can also be present here in the form of a lyophilizate, if appropriate together with excipients, and be dissolved before parenteral administration by addition of suitable solvents. Solutions such as are used, for example, for parental administration can also be used as infusion solutions. Preferred preservatives are, for example antioxidants, such as ascorbic acid, or microbicides, such as sorbic or benzoic acid.

Ointments are oil-in-water emulsions, which comprise not more than 70%, but preferably 20-50% of water or aqueous phase. The fatty phase consists, in particular, hydrocarbons, for example vaseline, paraffin oil or hard paraffin's, which preferably comprise suitable hydroxy compounds, such as fatty alcohol's or esters thereof, for example cetyl alcohol or wool wax alcohols, such as wool wax, to improve the water-binding capacity. Emulsifiers are corresponding lipophilic substances, such as sorbitan fatty acid esters (Spans), for example sorbitan oleate and/or sorbitan isostearate. Additives to the aqueous phase are, for example, humectants, such as polyalcohols, for example, glycerol, propylene glycol, sorbitol and/or polyethylene glycol, or preservatives and odoriferous substances.

Fatty ointments are anhydrous and comprise, as the base, in particular, hydrocarbons, for example paraffin, vaseline or paraffin oil, and furthermore naturally occurring or semisynthetic fats, for example, hydrogenated coconut-fatty acid triglycerides, or, preferably, hydrogenated oils, for example hydrogenated groundnut or castor oil, and furthermore fatty acid partial esters of glycerol, for example glycerol mono- and/or distearate, and for example, the fatty alcohols. They also can contain emulsifiers and/or additives mentioned in connection with the ointments which increase uptake of water.

Creams are oil-in-water emulsions, which comprise more than 50% of water. Oily bases used are, in particular, fatty alcohols, for example, lauryl, cetyl or stearyl alcohols, fatty acids, for example palmitic or stearic acid, liquid to solid waxes, for example isopropyl myristate, wool wax or beeswax, and/or hydrocarbons, for example vaseline (petrolatum) or paraffin oil. Emulsifiers are surface-active substances with predominantly hydrophilic properties, such as corresponding non-ionic emulsifiers, for example fatty acid esters of polyalcohols or ethyleneoxy adducts thereof, such as polyglyceric acid fatty acid esters or polyethylene sorbitan fatty esters (Tweens), and furthermore polyoxyethylene fatty alcohol ethers or polyoxyethylene fatty acid esters, or corresponding ionic emulsifiers, such as alkali metal salts of fatty alcohol sulfates, for example, sodium lauryl sulfate, sodium cetyl sulfate or sodium stearyl sulfate, which are usually used in the presence of fatty alcohols, for example cetyl stearyl alcohol or stearyl alcohol. Additives to the aqueous phase are, inter alia, agents which prevent the creams from drying out, for example polyalcohols, such as glycerol, sorbitol, propylene glycol and/or polyethylene glycols, and furthermore preservatives and odoriferous substances.

Pastes are creams and ointments having secretion-absorbing powder constituents, such as metal oxides, for example, titanium oxide or zinc oxide, and furthermore talc and/or aluminium silicates, which have the task of binding the moisture or secretions present.

Foams (i.e., liquid oil-in-water emulsions packaged in aerosol form) can be administered from pressurized containers. Propellant gases include halogenated hydrocarbons, such as polyhalogenated alkanes such as dichlorofluoromethane and dichlorotetrafluoroethane, or, preferably, non-halogenated gaseous hydrocarbons, air, $N_2O$, or carbon dioxide. The oily phases used are, inter alia, those mentioned above for ointments and creams, and the additives mentioned there are likewise used.

Tinctures and solutions usually comprise an aqueous-ethanolic base to which, humectants for reducing evaporation, such as polyalcohols (e.g., glycerol, glycols, polyethylene glycol) and re-oiling substances, such as fatty acid esters with lower polyethylene glycols (e.g., lipophilic substances soluble in the aqueous mixture) to substitute the fatty substances removed from the skin with the ethanol, and, if necessary or desired, other excipients and additives, are admixed.

The present invention further provides veterinary compositions comprising at least one active ingredient as above defined together with a veterinary carrier therefor. Veterinary carriers are materials for administering the composition and may be solid, liquid, or gaseous materials, which are inert or acceptable in the veterinary art and are compatible with the active ingredient. These veterinary compositions may be administered orally, parenterally, or by any other desired route.

The invention also relates to a process or method for treatment of the disease states mentioned above. The compounds can be administered prophylactically or therapeutically as such or in the form of pharmaceutical compositions, preferably in an amount, which is effective against the diseases mentioned. With a warm-blooded animal, for example, a human requiring such treatment, the compounds are used, in particular, in the form of pharmaceutical composition. A daily dose of about 0.1 to about 5 g, preferably 0.5 g to about 2 g, of a compound of the present invention is administered here for a body weight of about 70 kg.

EXAMPLES OF CARRYING OUT THE INVENTION

Figure 1:
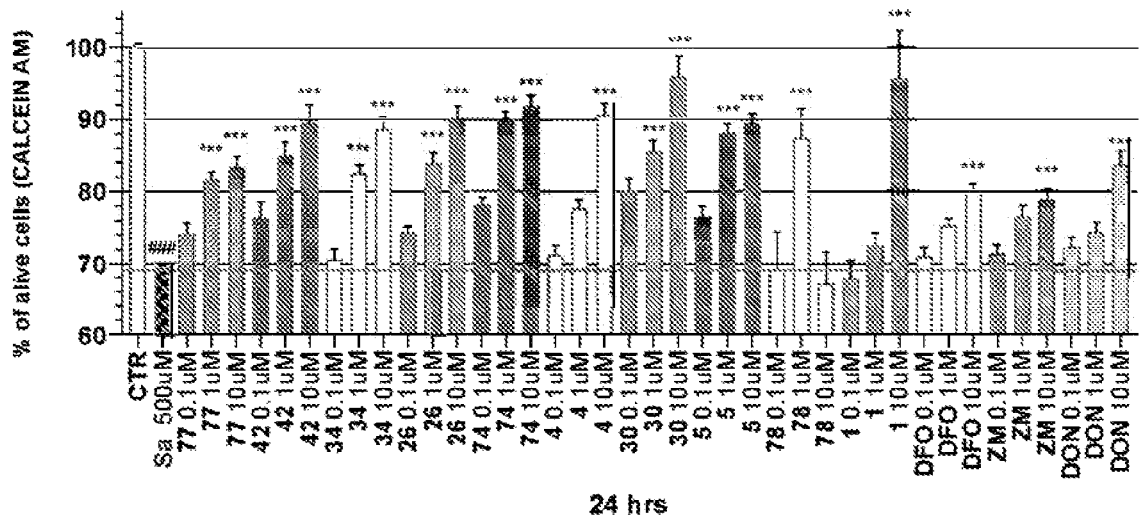
FIG. 1 shows neuroprotective effect of novel compounds in salsolinol-induced model of Parkinson's disease. Along with the compounds of the invention, Donepezil (DON), Deferoxamine (DFO) and ZM241385 (ZM) were used as positive controls at 0.1, 1 and 10 µM. All results are presented as mean±the standard error of the mean (SEM) in triplicate experiments (n=9) in three separated days. ANOVA, Bonferonni post hoc test; *, # $P<0.05$; , ## $P<0.01$; *, ### $P<0.001$; *P compared with vehicle with 500 µM salsolinol, # P compared with vehicle without Salsolinol 500 µM. A value of $P<0.05$ is considered statistically significant.
Figure 2:
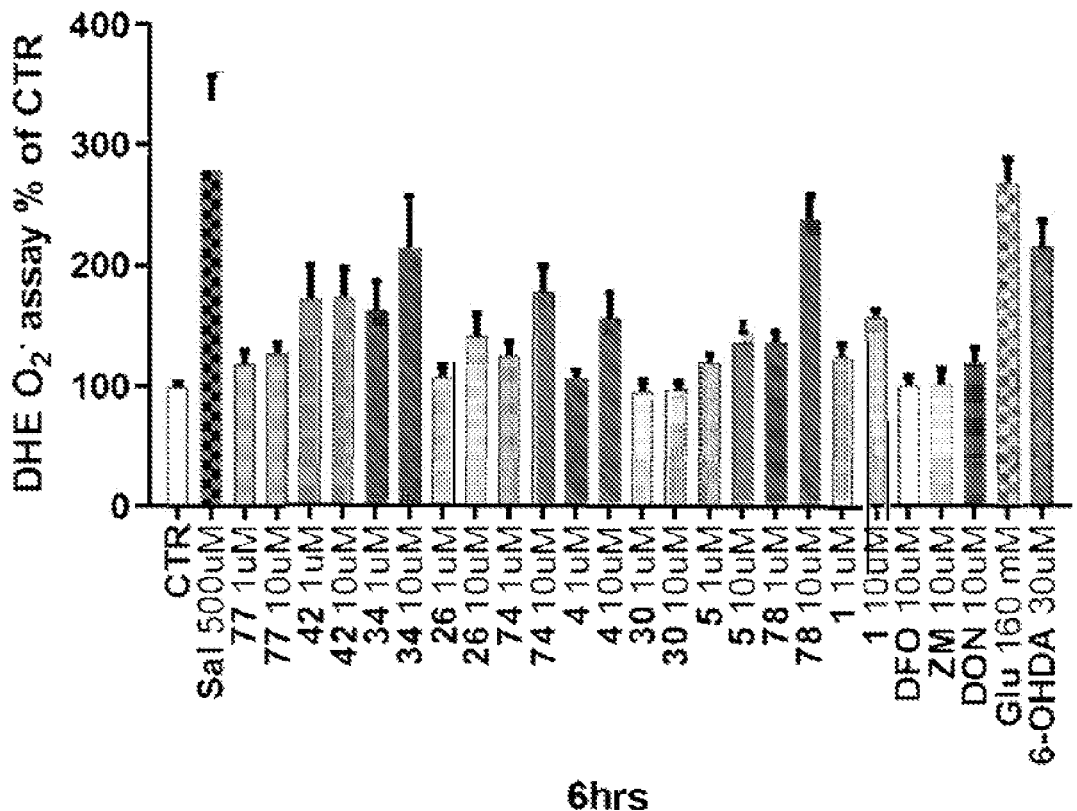
FIG. 2 Effects of novel compounds on salsolinol-induced oxidative stress. Examples were tested in active concentrations 1 µM and 10 µM along with positive controls DON, DFO and ZM (10 µM), and negative controls OS-inducer 6-hydroxydopamine (6-OHDA) and glutamate (Glu). All results are present mean±the standard error of the mean (SEM) in triplicate experiments (n=9) in three separated days.

The following examples serve to illustrate the invention without limiting the scope thereof. Unless otherwise stated, all percentages and the like amounts are based on weight. The starting materials may be obtained from commercial sources (Sigma, Aldrich, Fluka, etc.) or can be prepared as described below.

Thin-layer chromatography was carried out on Silica 60 $F_{254}$ plates (Merck) using petroleum ether/ethyl acetate as a developing system and the spots were detected by UV light (254 nm). The column chromatography purification was carried out by silica Davisil 40-63 micron (Grace Davision).

The chromatographic purity and mass of prepared compounds was determined using an Alliance 2695 separation module (Waters) linked simultaneously to a DAD detector PDA 996 (Waters) and a Q-Tof micro (Waters) benchtop quadrupole orthogonal acceleration time-of-flight tandem mass spectrometer. Samples were dissolved in DMSO and diluted to a concentration of 10 µg/mL in initial mobile phase. The samples (10 µL) were injected on a RP-column Symmetry C18 (150 mm×2.1 mm×3.5 µm, Waters) and separated at a flow rate of 0.2 mL/min with following binary gradient: 0 min, 10% B; 0-24 min, a linear gradient to 90% B, followed by 10 min isocratic elution of 90% B. At the end of the gradient, the column was re-equilibrated to initial conditions. 15 mM formic acid adjusted to pH 4.0 by ammonium hydroxide was used as solvent (A) and methanol as the organic modifier (solvent B). The eluent was introduced into the DAD (scanning range 210-400 nm, with 1.2 nm resolution) and an ESI source (source temperature 110° C., capillary voltage +3.0 kV, cone voltage +20 V, desolvation temperature 250° C.). Nitrogen was used both as desolvation gas (500 L/h) as well as cone gas (50 L/h). The data was obtained in positive (ESI+) ionization mode in the 50-1000 m/z range.

Elemental analysis was determined using Flash EA 1112 analyser (Thermo Scientific). The values were obtained as an average of three measurements.

$^1$H and $^{13}$C NMR spectra were recorded on Jeol ECA-500 operating at a frequency of 500 MHz ($^1$H) and 125 MHz ($^{13}$C). Samples were prepared by dissolving substances in DMSO-$d_6$ or CDCl$_3$ and chemical shifts were calibrated to residual solvent peak (DMSO-$d_5$-2.49 ppm, CHCl$_3$-7.26 for proton) and DMSO-$d_6$ or CDCl$_3$ (DMSO-$d_6$-39.5 ppm and CDCl$_3$-77.0 for carbon).

C2,C6-disubstituted-9-(subst.)benzyl-9H-purine derivatives were prepared from 2,6-dichloro-9H-purine. Firstly, benzyl substituents were introduced to the N9-position of purine moiety either by reaction of 2,6-dichloro-9H-purine with the corresponding benzyl halide in the presence of potassium carbonate in dry N,N-dimethylformamide or by reaction with the corresponding benzyl alcohol using Mitsunobu reaction. In the case of C2,C6-symmetric compounds, the substituents at C2 and C6 position were introduced simultaneously by heating of 2,6-dichloro-9-benzylated-9H-purine with an excess of appropriate cyclic amine and Hünig's base at 165° C. C2,C6-assymmetric compounds were prepared in two steps, firstly by nucleophilic substitution at C6 position by the reaction of 2,6-dichloro-9-benzylated-9H-purine with cyclic amine and triethylamine in refluxing propanol and later by substitution at C2 position using same conditions as for synthesis of C2,C6-symmetric compounds.

Modification of Purines at N9-Position:

A) Reaction of 2,6-dichloropurine with Benzyl Halides 2,6-Dichloro-9H-purine (2 g, 10.58 mmol) and potassium carbonate (4.39 g, 31.74 mmol) were suspended under argon in dry N,N-dimethylformamide (53 mL) and stirred at room temperature for 30 minutes. Thereafter, benzylhalogenide (12.70 mmol) was dropwise added and resulting mixture was stirred at room temperature for 16 h. Resulting suspension was poured into ice cold water (300 mL) and extracted by ethyl acetate (6×30 mL). Combined organic layers were washed with brine (2×50 mL), dried (Na$_2$SO$_4$) and concentrated under reduced pressure. N9-isomer was obtained by silica column chromatography using petroleum ether/ethyl acetate as a mobile phase, starting from 4:1 with ethyl acetate gradient.

Example 1—9-Benzyl-2,6-dichloro-9H-purine

Prepared from 2,6-dichloropurine and benzyl bromide. White solid, chemical formula: $C_{12}H_8Cl_2N_4$, yield (%): 53. HPLC-UV/VIS retention time, purity (min., %): 26.18, 98.0. ESI$^+$-MS m/z (rel. int. %, ion): 279.4 (100, [$^{35}$Cl-M+H]$^+$), 281.4 (79, [$^{37}$Cl-M+H]$^+$). EA (% C, % H, % N, calc./found): 51.64/51.19, 2.89/2.54, 20.07/19.43. $^1$H-NMR (500 MHz, DMSO-$d_6$) δ (ppm): 5.49 (s, 2H), 7.29-7.37 (m, 5H), 8.83 (s, 1H). $^{13}$C-NMR (125 MHz, DMSO-$d_6$) δ (ppm): 47.0, 127.6 (2×C), 128.0, 128.7 (2×C), 130.4, 135.6, 148.3, 149.8, 151.1, 153.3.

Example 2—2,6-Dichloro-9-(2,6-dichlorobenzyl)-9H-purine

Prepared from 2,6-dichloropurine and 2,6-dichlorobenzyl bromide. White solid, chemical formula: $C_{12}H_6Cl_4N_4$, yield (%): 55. HPLC-UV/VIS retention time, purity (min., %): 27.75, 98.5%. ESI$^+$-MS m/z (rel. int. %, ion): 347.4 [$^{35}$Cl- M+H]⁺), 349.4 (79, [³⁷Cl-M+H]⁺). EA (% C, % H, % N, calc./found): 41.41/41.65, 1.74/1.59, 16.10/16.49. ¹H-NMR (500 MHz, DMSO-d₆) δ (ppm): 5.67 (s, 2H), 7.47 (dd, J=8.9, 7.3 Hz, 1H), 7.57 (d, J=7.9 Hz, 2H), 8.61 (s, 1H). ¹³C-NMR (125 MHz, DMSO-d₆) δ (ppm): 43.7, 129.1 (2×C), 129.5, 130.2, 131.8, 136.1 (2×C), 148.2, 149.8, 151.1, 153.4.

B) Reaction of 2,6-dichloropurine with Benzyl Alcohols Under Mitsunobu Conditions DIAD (1.2 eq.) was under argon atmosphere dropwise added to a solution of 2,6-dichloro-9H-purine (0.5 g), aralkyl alcohol (1.2 eq.) and triphenylphosphine (1.2 eq.) in dry THF (18 mL). Reaction mixture was stirred at room temperature for 1 h and concentrated under reduced pressure. Majority of triphenylphosphine oxide side product was removed by crystallization from hot toluene (10 mL). The crude material was later purified by silica column chromatography using petroleum ether/ethyl acetate as a mobile phase, starting from 5:1 with ethyl acetate gradient.

Example 3—2,6-Dichloro-9-(2-methoxybenzyl)-9H-purine

Prepared from 2,6-dichloropurine and 2-methoxybenzyl alcohol. White solid, chemical formula: $C_{13}H_{10}Cl_2N_4O$, yield (%): 49. HPLC-UV/VIS retention time, purity (min., %): 26.25, 98.9. ESI³⁰-MS m/z (rel. int. %, ion): 309.4 (100, [³⁵Cl-M+H]⁺), 311.4 (78, [³⁷Cl-M+H]⁺). EA (% C, % H, % N, calc./found): 55.51/54.88, 3.26/3.59, 18.12/17.51 ¹H-NMR (500 MHz, DMSO-d₆) δ (ppm): 3.80 (s, 3H), 5.40 (s, 2H), 6.91 (td, J=7.4, 1.0 Hz, 1H), 7.03 (d, J=8.3 Hz, 1H), 7.13 (dd, J=7.3, 1.5 Hz, 1H), 7.32 (td, J=7.9, 1.5 Hz, 1H), 8.70 (s, 1H). ¹³C-NMR (125 MHz, DMSO-d₆) δ (ppm): 43.3, 55.5, 111.1, 120.4, 122.9, 129.3, 129.9, 130.3, 148.8, 149.7, 150.9, 153.5, 156.9.

Example 4—2,6-Dichloro-9-(2-chlorobenzyl)-9H-purine

Prepared from 2,6-dichloropurine and 2-chlorobenzyl alcohol. White solid, chemical formula: $C_{12}H_7Cl_3N_4$, yield (%): 53. HPLC-UV/VIS retention time, purity (min., %): 27.23, 97.2. ESI³⁰-MS m/z (rel. int. %, ion): 313.4 (99, [³⁵Cl-M+H]⁺), 315.4 (100, [³⁷Cl-M+H]⁺). EA (% C, % H, % N, calc./found): 45.96/45.87, 2.25/2.19, 17.87/18.12. ¹H-NMR (500 MHz, DMSO-d₆) δ (ppm): 5.57 (s, 2H), 7.14 (dd, J=7.6, 1.2 Hz, 1H), 7.30 (td, J=7.6, 1.0 Hz, 1H), 7.37 (td, J=7.7, 1.6 Hz, 1H), 7.52 (dd, J=7.9, 0.9 Hz, 1H), 8.77 (s, 1H). ¹³C-NMR (125 MHz, DMSO-d₆) δ (ppm): 45.3, 127.7, 129.7 (2×C), 130.1, 130.5, 132.1, 132.6, 148.6, 149.9, 151.2, 153.6.

Example 5—9-(2-Bromobenzyl)-2,6-dichloro-9H-purine

Prepared from 2,6-dichloropurine and 2-bromobenzyl alcohol. White solid, chemical formula: $C_{12}H_7BrCl_2N_4$, yield (%): 62. HPLC-UV/VIS retention time, purity (min., %): 23.08, 97.1. ESI³⁰-MS m/z (rel. int. %, ion): 357.1 (100, [³⁵Cl-³⁵Cl-⁷⁹Br-M+H]⁺), 359.0 (97, [³⁵Cl-³⁷Cl-⁷⁹Br-M+H]⁺, [³⁵Cl-³⁵Cl-⁸¹Br-M+H]⁺), 361.0 (62, [³⁷Cl-³⁷Cl-⁷⁹Br-M+H]⁺, [³⁵Cl-³⁷Cl-⁸¹Br-M+H]⁺). EA (% C, % H, % N, calc./found): 40.26/40.33, 1.97/2.23, 15.65/15.32.

¹H-NMR (500 MHz, DMSO-d₆) δ (ppm): 5.53 (s, 2H), 7.05 (dd, J=7.5, 1.7 Hz, 1H), 7.30 (td, J=7.6, 1.8 Hz, 1H), 7.34 (td, J=7.5, 1.4 Hz, 1H), 7.70 (dd, J=7.8, 1.4 Hz, 1H), 8.76 (s, 1H). ¹³C-NMR (125 MHz, DMSO-d₆) δ (ppm): 47.6, 122.2, 128.3, 129.5, 130.3, 130.5, 132.9, 134.2, 148.6, 149.9, 151.2, 153.6.

TABLE 1

Examples of 2,6-dichloro-9-(benzylated)-9H-purine derivatives

| Comp. | PURINE SUBSTITUENT N9 | CHN ANALYSIS [% C, % H, % N] [calc./found] | MS ANALYSIS [M + H]⁺ |
|---|---|---|---|
| 1 | 2-methylbenzyl | 53.26/53.48, 3.44/3.66, 19.11/19.35 | 293 |
| 2 | 3-methylbenzyl | 53.26/53.32, 3.44/3.61, 19.11/19.05 | 293 |
| 3 | 4-methylbenzyl | 53.26/53.30, 3.44/3.26, 19.11/19.00 | 293 |
| 4 | 2-hydroxybenzyl | 48.84/49.05, 2.73/2.91, 18.98/19.17 | 295 |
| 5 | 3-hydroxybenzyl | 48.84/48.64, 2.73/2.69, 18.98/18.62 | 295 |
| 6 | 4-hydroxybenzyl | 48.84/48.77, 2.73/2.45, 18.98/18.59 | 295 |
| 7 | 3-methoxybenzyl | 50.51/50.55, 3.26/3.29, 18.12/18.20 | 309 |
| 8 | 4-methoxybenzyl | 50.51/50.23, 3.26/3.48, 18.12/18.49 | 309 |
| 9 | 2-fluorobenzyl | 48.51/48.61, 2.37/2.43, 18.86/19.12 | 297 |
| 10 | 3-fluorobenzyl | 48.51/48.62, 2.37/2.46, 18.86/19.05 | 297 |
| 11 | 4-fluorobenzyl | 48.51/48.33, 2.37/2.49, 18.86/18.61 | 297 |
| 12 | 3-chlorobenzyl | 45.96/45.83, 2.25/2.12, 17.87/17.98 | 312 |
| 13 | 4-chlorobenzyl | 45.96/46.29, 2.25/2.41, 17.87/18.03 | 312 |
| 14 | 3-bromobenzyl | 40.26/40.00, 1.97/2.06, 15.65/15.38 | 356 |
| 15 | 4-bromobenzyl | 40.26/40.51, 1.97/1.79, 15.65/15.83 | 356 |

Synthesis of C2,C6-Symmetric Compounds

9-Benzylated-2,6-dichloro-9H-purine (0.485 mmol) was heated with corresponding cyclic amine (7.28 mmol) and Hünig's base (422 μl, 2.43 mmol) at 165° C. for 4 h. The mixture was diluted with water (10 mL) and extracted by chloroform (4×10 mL). Combined organic layers were washed with brine (10 mL), dried (Na₂SO₄) and concentrated under reduced pressure. Crude material was purified by silica column chromatography using petroleum ether/ethyl acetate, starting from 5:1 with ethyl acetate gradient.

Example 6—9-Benzyl-2,6-di(piperidin-1-yl)-9H-purine

Prepared from 9-benzyl-2,6-dichloro-9H-purine and piperidine. White solid, chemical formula: $C_{22}H_{28}N_6$, yield (%): 70. HPLC-UV/VIS retention time, purity (min., %): 35.30, 99.9. ESI³⁰-MS m/z (rel. int. %, ion): 377.1 (100, [M+H]⁺). EA (% C, % H, % N, calc./found): 70.18/69.43, 7.50/7.78, 22.32/21.94. ¹H NMR (500 MHz, DMSO-d₆) δ

(ppm): 1.47-1.48 (m, 4H), 1.52-1.53 (m, 6H), 1.62 (s, 2H), 3.66 (s, 4H), 4.07 (bs, 4H), 5.19 (s, 2H), 7.25-7.26 (m, 1H), 7.29-7.32 (m, 4H), 7.85 (s, 1H). $^{13}$C-NMR (125 MHz, DMSO-d$_6$) δ (ppm): 24.4, 24.5, 25.2 (2×C), 25.6 (2×C), 44.9, 45.3 (2×C), 45.7 (2×C), 112.8, 127.6, 127.8 (2×C), 128.5 (2×C), 136.6, 137.5, 152.8, 153.2, 158.1.

Example 7—9-(3-Hydroxybenzyl)-2,6-di(pyrrolidin-1-yl)-9H-purine

Prepared from 2,6-dichloro-9-(3-hydroxybenzyl)-9H-purine and pyrrolidine. White solid, chemical formula: $C_{20}H_{24}N_6O$, yield (%): 72. HPLC-UV/VIS retention time, purity (min., %): 29.03, 98.2. ESI$^+$-MS m/z (rel. int. %, ion): 365.7 (100, [M+H]$^+$). EA (% C, % H, % N, calc./found): 65.91/65.67, 6.64/6.42, 23.06/23.28. $^1$H-NMR (500 MHz, DMSO-d$_6$) δ (ppm): 1.84-1.87 (m, 8H), 3.45-3.47 (m, 4H), 3.59 (bs, 2H), 3.95 (bs, 2H), 5.10 (s, 2H), 6.63-6.64 (m, 2H), 6.73 (d, J=7.3 Hz, 1H), 7.09 (t, J=7.8 Hz, 1H), 7.74 (s, 1H), 9.40 (s, 1H). $^{13}$C-NMR (125 MHz, DMSO-d$_6$) δ (ppm): 23.6, 25.1 (2×C), 25.8, 45.4, 46.4 (3×C), 48.1, 113.2, 114.3, 114.4, 118.1, 129.5, 136.7, 139.2, 152.4, 152.6, 157.4, 157.5.

Example 8—9-(2-Methoxybenzyl)-2,6-dimorpholino-9H-purine

Prepared from 2,6-dichloro-9-(2-methoxybenzyl)-9H-purine and morpholine. White solid, chemical formula: $C_{21}H_{26}N_6O_3$, yield (%): 88. HPLC-UV/VIS retention time, purity (min., %): 27.90, 99.9. ESI$^{30}$-MS m/z (rel. int. %, ion): 411.8 (100, [M+H]$^+$). EA (% C, % H, % N, calc./found): 61.45/61.39, 6.38/6.11, 20.47/20.59. $^1$H-NMR (500 MHz, DMSO-d$_6$) δ (ppm): 3.60 (bs, 8H), 3.66 (bs, 4H), 3.82 (s, 3H), 4.10 (bs, 4H), 5.15 (s, 2H), 6.86 (t, J=7.2 Hz, 1H), 6.99-7.02 (m, 2H), 7.26 (t, J=7.3 Hz, 1H), 7.80 (s, 1H). $^{13}$C-NMR (125 MHz, DMSO-d$_6$) δ (ppm): 41.4, 44.7 (2×C), 45.1 (2×C), 55.5, 66.1 (2×C), 66.2, 110.9, 113.3, 120.3, 124.6, 129.1, 129.3, 137.9, 152.9, 153.3, 156.8, 158.0.

Example 9—9-(2-Bromobenzyl)-2,6-dithiomorpholino-9H-purine

Prepared from 9-(2-bromobenzyl)-2,6-dichloro-9H-purine and thiomorpholine. Pale yellow solid, chemical formula: $C_{20}H_{23}BrN_6S_2$, yield (%): 65. HPLC-UV/VIS retention time, purity (min., %): 35.67, 99.9. ESI$^{30}$-MS m/z (rel. int. %, ion): 491.9 (87, [$^{79}$Br-M+H]$^+$), 493.9 (100, [$^{81}$Br-M+H]$^+$). EA (% C, % H, % N, calc./found): 48.88/48.85, 4.72/4.77, 17.10/17.15. $^1$H-NMR (500 MHz, DMSO-d$_6$) δ (ppm): 2.49-2.51 (m, 4H), 2.64-2.66 (m, 4H), 3.95-3.97 (m, 4H), 4.39 (bs, 4H), 5.29 (s, 2H), 7.15 (dd, J=7.6, 1.2 Hz, 1H), 7.24 (td, J=7.6, 1.4 Hz, 1H), 7.33 (t, J=7.2 Hz, 1H), 7.64 (d, J=7.0 Hz, 1H), 7.92 (s, 1H). $^{13}$C-NMR (125 MHz, DMSO-d$_6$) δ (ppm): 25.6 (2×C), 26.3 (2×C), 46.4, 46.6 (3×C), 47.3, 112.9, 122.6, 127.9, 129.9, 130.3, 132.7, 135.7, 137.7, 153.1, 153.1, 157.3.

Example 10—9-(2,6-Dichlorobenzyl)-2,6-di(pyrrolidine-1-yl)-9H-purine

Prepared from 9-(2,6-dichlorobenzyl)-2,6-dichloro-9H-purine and pyrrolidine. White solid, chemical formula: $C_{20}H_{22}Cl_2N_6$, yield (%): 46. HPLC-UV/VIS retention time, purity (min., %): 35.37, 99.9. ESI$^{30}$-MS m/z (rel. int. %, ion): 417.8 (99, [$^{35}$Cl-M+H]$^+$), 419.8 (100, [$^{37}$Cl-M+H]$^+$). EA (% C, % H, % N, calc./found): 57.56/57.58, 5.31/5.33, 20.14/20.10. $^1$H-NMR (500 MHz, DMSO-d$_6$) δ (ppm): 1.81-1.87 (m, 8H), 3.36-3.38 (m, 4H), 3.55 (bs, 2H), 3.91 (bs, 2H), 5.38 (s, 2H), 7.38 (dd, J=8.6, 7.6 Hz, 1H), 7.49 (d, J=7.9 Hz, 2H), 7.54 (s, 1H).
$^{13}$C-NMR (125 MHz, DMSO-d$_6$) δ (ppm): 23.7, 25.1 (2×C), 25.8, 42.4, 46.2 (3×C), 48.0, 112.9, 128.7 (2×C), 130.8, 131.1, 136.0, 136.6 (2×C), 152.3, 152.5, 157.0.

TABLE 2

Examples of prepared C2,C6-symmetric 9-(benzylated)-9H-purine derivatives

| | PURINE SUBSTITUENT | | CHN ANALYSIS [% C, % H, % N] [calc./found] | MS ANALYSIS [M + H]$^+$ |
|---|---|---|---|---|
| Comp. | C2, C6 | N9 | | |
| 1 | azetidin-1-yl | benzyl | 67.48/67.23, 6.29/6.42, 26.23/26.30 | 321 |
| 2 | pyrrolidin-1-yl | benzyl | 68.94/68.87, 6.94/6.63, 24.12/24.48 | 349 |
| 3 | azepan-1-yl | benzyl | 71.25/71.15, 7.97/8.02, 20.77/20.79 | 405 |
| 4 | morpholin-4-yl | benzyl | 63.14/63.32, 6.36/6.15, 22.09/22.19 | 381 |
| 5 | thiomorpholin-4-yl | benzyl | 58.22/57.84, 5.86/5.59, 20.37/20.25 | 413 |
| 6 | piperazin-1-yl | benzyl | 63.47/63.58, 6.92/6.86, 29.61/29.50 | 379 |
| 7 | 4-methylpiperazin-1-yl | benzyl | 65.00/64.63, 7.44/7.29, 27.56/28.01 | 407 |
| 8 | piperazin-1-yl | 2-methylbenzyl | 64.26/63.98, 7.19/7.36, 28.55/28.73 | 393 |
| 9 | pyrrolidin-1-yl | 2-methylbenzyl | 69.58/69.35, 7.23/7.11, 23.19/23.51 | 363 |
| 10 | azetidin-1-yl | 2-methylbenzyl | 68.24/68.49, 6.63/6.82, 25.13/24.69 | 335 |
| 11 | thiomorpholin-4-yl | 2-methylbenzyl | 59.12/58.87, 6.14/6.45, 19.70/19.32 | 427 |
| 12 | piperidin-1-yl | 2-methylbenzyl | 70.74/71.02, 7.74/7.76, 21.52/21.16 | 391 |
| 13 | morpholin-4-yl | 3-methylbenzyl | 63.94/63.66, 6.64/6.61, 21.30/21.69 | 395 |
| 14 | piperazin-1-yl | 3-methylbenzyl | 64.26/64.25, 7.19/7.25, 28.55/28.48 | 393 |
| 15 | pyrrolidin-1-yl | 3-methylbenzyl | 69.58/69.64, 7.23/7.28, 23.19/23.28 | 363 |
| 16 | azepan-1-yl | 3-methylbenzyl | 71.74/71.75, 8.19/8.26, 20.08/19.96 | 419 |
| 17 | piperidin-1-yl | 4-methylbenzyl | 70.74/70.60, 7.74/7.81, 21.52/21.61 | 391 |
| 18 | azetidin-1-yl | 4-methylbenzyl | 68.24/68.15, 6.63/6.54, 25.13/25.31 | 335 |
| 19 | morpholin-4-yl | 4-methylbenzyl | 63.94/63.98, 6.64/6.87, 21.30/21.06 | 395 |
| 20 | pyrrolidin-1-yl | 4-methylbenzyl | 69.58/69.89, 7.23/7.17, 23.19/22.97 | 363 |
| 21 | morpholin-4-yl | 2-hydroxybenzyl | 60.59/60.46, 6.10/6.18, 21.20/21.49 | 397 |
| 22 | piperidin-1-yl | 2-hydroxybenzyl | 67.32/67.46, 7.19/7.01, 21.41/21.69 | 393 |
| 23 | pyrrolidin-1-yl | 2-hydroxybenzyl | 65.91/65.73, 6.64/6.89, 23.06/22.77 | 365 |
| 24 | piperazin-1-yl | 2-hydroxybenzyl | 60.89/60.77, 6.64/6.36, 28.41/28.22 | 395 |
| 25 | azetidin-1-yl | 3-hydroxybenzyl | 64.27/64.43, 5.99/6.06, 24.98/24.86 | 337 |
| 26 | pyrrolidin-1-yl | 3-hydroxybenzyl | 65.91/65.83, 6.64/6.48, 23.06/23.28 | 365 |

TABLE 2-continued

Examples of prepared C2,C6-symmetric 9-(benzylated)-9H-purine derivatives

| Comp. | PURINE SUBSTITUENT C2, C6 | N9 | CHN ANALYSIS [% C, % H, % N] [calc./found] | MS ANALYSIS [M + H]+ |
|---|---|---|---|---|
| 27 | 4-methylpiperazin-1-yl | 3-hydroxybenzyl | 62.54/62.81, 7.16/7.26, 26.52/26.48 | 423 |
| 28 | thiomorpholin-4-yl | 3-hydroxybenzyl | 56.05/56.00, 5.64/5.61, 19.61/19.83 | 429 |
| 29 | piperidin-1-yl | 3-hydroxybenzyl | 67.32/67.17, 7.19/7.35, 21.41/21.68 | 393 |
| 30 | pyrrolidin-1-yl | 4-hydroxybenzyl | 65.91/66.18, 6.64/6.68, 23.06/23.15 | 365 |
| 31 | morpholin-4-yl | 4-hydroxybenzyl | 60.59/60.41, 6.10/6.15, 21.20/21.28 | 397 |
| 32 | azetidin-1-yl | 4-hydroxybenzyl | 64.27/64.33, 5.99/6.13, 24.98/24.68 | 337 |
| 33 | azepan-1-yl | 4-hydroxybenzyl | 68.54/68.93, 7.67/7.49, 19.98/20.21 | 421 |
| 34 | piperazin-1-yl | 4-hydroxybenzyl | 60.89/61.15, 6.64/6.55, 28.41/28.11 | 395 |
| 35 | pyrrolidin-1-yl | 2-methoxybenzyl | 66.64/66.82, 6.92/6.84, 22.21/22.08 | 379 |
| 36 | azetidin-1-yl | 2-methoxybenzyl | 65.12/65.34, 6.33/6.47, 23.98/22.76 | 351 |
| 37 | 4-methylpiperazin-1-yl | 2-methoxybenzyl | 63.28/63.35, 7.39/7.65, 25.67/25.20 | 437 |
| 38 | thiomorpholin-4-yl | 3-methoxybenzyl | 56.99/56.77, 5.92/6.14, 18.99/19.26 | 443 |
| 39 | piperidin-1-yl | 3-methoxybenzyl | 67.95/67.61, 7.44/7.35, 20.67/20.83 | 407 |
| 40 | azepan-1-yl | 3-methoxybenzyl | 69.09/69.42, 7.89/7.63, 19.34/19.65 | 435 |
| 41 | piperazin-1-yl | 3-methoxybenzyl | 61.74/61.63, 6.91/7.15, 27.43/27.37 | 409 |
| 42 | pyrrolidin-1-yl | 3-methoxybenzyl | 66.64/66.32, 6.92/7.23, 22.21/22.56 | 379 |
| 43 | morpholin-4-yl | 4-methoxybenzyl | 61.45/61.24, 6.38/6.63, 20.47/20.29 | 411 |
| 44 | piperidin-1-yl | 4-methoxybenzyl | 67.95/68.13, 7.44/7.16, 20.67/20.81 | 407 |
| 45 | azetidin-1-yl | 4-methoxybenzyl | 65.12/65.03, 6.33/6.28, 23.98/23.81 | 351 |
| 46 | pyrrolidin-1-yl | 4-methoxybenzyl | 66.64/66.56, 6.92/7.01, 22.21/22.13 | 379 |
| 47 | piperazin-1-yl | 2-fluorobenzyl | 60.59/60.38, 6.36/6.49, 28.26/28.56 | 396 |
| 48 | azetidin-1-yl | 2-fluorobenzyl | 63.89/63.61, 5.66/5.72, 24.84/24.91 | 338 |
| 49 | morpholin-4-yl | 2-fluorobenzyl | 60.29/60.35, 5.82/5.68, 21.09/21.22 | 398 |
| 50 | pyrrolidin-1-yl | 3-fluorobenzyl | 65.55/65.60, 6.33/6.40, 22.93/23.01 | 366 |
| 51 | azepan-1-yl | 3-fluorobenzyl | 68.22/68.00, 7.93/8.15, 19.89/20.13 | 422 |
| 52 | piperazin-1-yl | 4-fluorobenzyl | 60.59/60.68, 6.36/6.21, 28.26/28.39 | 396 |
| 53 | thiomorpholin-4yl | 4-fluorobenzyl | 55.79/55.77, 5.38/5.36, 19.52/19.55 | 430 |
| 54 | piperidin-1-yl | 4-fluorobenzyl | 66.98/66.71, 6.90/6.82, 21.30/21.44 | 394 |
| 55 | 4-methylpiperazin-1-yl | 4-fluorobenzyl | 62.24/62.38, 6.89/7.21, 26.40/26.22 | 424 |
| 56 | piperidin-1-yl | 2-chlorobenzyl | 64.30/64.61, 6.62/6.35, 20.45/20.34 | 411 |
| 57 | morpholin-4-yl | 2-chlorobenzyl | 57.90/57.96, 5.59/5.70, 20.26/20.44 | 415 |
| 58 | piperazin-1-yl | 2-chlorobenzyl | 58.17/58.15, 6.10/6.10, 27.14/27.18 | 413 |
| 59 | 4-methylpiperazin-1-yl | 2-chlorobenzyl | 59.92/60.05, 6.63/6.78, 25.41/25.39 | 441 |
| 60 | azetidin-1-yl | 3-chlorobenzyl | 60.93/60.85, 5.40/5.27, 23.68/23.84 | 354 |
| 61 | pyrrolidin-1-yl | 3-chlorobenzyl | 62.74/62.57, 6.05/5.87, 21.95/22.09 | 382 |
| 62 | azepan-1-yl | 4-chlorobenzyl | 65.66/65.48, 7.12/6.98, 19.14/19.05 | 438 |
| 63 | thiomorpholin-4-yl | 4-chlorobenzyl | 53.74/53.86, 5.19/5.01, 18.80/18.99 | 447 |
| 64 | piperazin-1-yl | 4-chlorobenzyl | 58.17/58.15, 6.10/6.10, 27.14/27.18 | 413 |
| 65 | azepan-1-yl | 2-bromobenzyl | 59.63/59.75, 6.46/6.51, 17.38/17.46 | 483 |
| 66 | piperidin-1-yl | 2-bromobenzyl | 58.02/57.98, 5.98/6.21, 18.45/18.65 | 455 |
| 67 | 4-methylpiperazin-1-yl | 2-bromobenzyl | 54.43/54.52, 6.02/6.14, 23.08/22.76 | 485 |
| 68 | pyrrolidin-1-yl | 3-bromobenzyl | 56.21/56.22, 5.42/5.40, 19.67/19.78 | 427 |
| 69 | thiomorpholin-4-yl | 3-bromobenzyl | 48.88/45.01, 4.72/4.51, 17.10/16.83 | 491 |
| 70 | azepan-1-yl | 4-bromobenzyl | 59.63/59.77, 6.46/6.53, 17.38/17.41 | 483 |
| 71 | morpholin-4-yl | 4-bromobenzyl | 52.30/52.49, 5.05/4.81, 18.30/18.56 | 459 |
| 72 | piperidin-1-yl | 4-bromobenzyl | 58.02/58.20, 5.98/6.13, 18.45/18.21 | 455 |
| 73 | azetidin-1-yl | 2,6-dichlorobenzyl | 55.54/55.68, 4.66/4.71, 21.59/21.36 | 389 |
| 74 | pyrrolidin-1-yl | 2,6-dichlorobenzyl | 57.56/57.48, 5.31/5.33, 20.14/19.87 | 418 |
| 75 | piperazin-1-yl | 2,6-dichlorobenzyl | 53.70/53.61, 5.41/5.38, 25.05/25.17 | 447 |
| 76 | morpholin-4-yl | 2,6-dichlorobenzyl | 53.46/53.56, 4.94/5.06, 18.70/18.92 | 449 |

Synthesis of C2,C6-Assymmetric Compounds:

A) Nucleophilic Substitution at Purine C6-Position

Suspension of 9-benzylated-2,6-dichloro-9H-purine (0.717 mmol), cyclic amine (0.860 mmol) and triethylamine (250 µl, 1,793 mmol) was refluxed in n-propanol (7.17 mL) for 4 h. Subsequently, the reaction mixture was concentrated under reduced pressure and the residue was diluted with water (15 mL) and extracted by ethyl acetate (5×10 mL). Combined organic layers were washed with brine (15 mL), dried ($Na_2SO_4$) and concentrated under reduced pressure. Crude material was purified by silica column chromatography using petroleum ether/ethyl acetate, starting from 8:1 with ethyl acetate gradient.

Example 11—9-Benzyl-2-chloro-6-(piperidin-1-yl)-9H-purine

Colourless oil, chemical formula: $C_{17}H_{18}ClN_5$, yield (%): 98. HPLC-UV/VIS retention time, purity (min., %): 29.65, 99.4. ESI[30]-MS m/z (rel. int. %, ion): 328.6 (100, [$^{35}$Cl-M+H]+), 330.6 (52, [$^{37}$Cl-M+H]+). EA (% C, % H, % N, calc./found): 62.29/61.92, 5.53/5.73, 21.36/20.97. $^1$H-NMR (500 MHz, DMSO-$d_6$) δ (ppm): 1.55 (s, 4H), 1.61-1.64 (m, 2H), 3.83 (s, 2H), 4.43 (bs, 2H), 5.33 (s, 2H), 7.25-7.34 (m, 5H), 8.26 (s, 1H). $^{13}$C-NMR (125 MHz, DMSO-$d_6$) δ (ppm): 24.0, 25.6 (2×C), 44.5, 46.2, 46.8, 117.8, 127.4 (2×C), 127.8, 128.7 (2×C), 136.7, 140.1, 151.6, 152.8, 153.2.

B) Nucleophilic Substitution at Purine C2-Position

9-Benzylated-2-chloro-6-substituted-9H-purine (0.342 mmol) was heated with cyclic amine (15 eq.) and Hünig's base (5 eq.) at 165° C. for 4 h. The mixture was diluted with water (10 mL) and extracted by chloroform (5×10 mL). Combined organic layers were washed with brine (10 mL), dried ($Na_2SO_4$) and concentrated under reduced pressure. Crude material was purified by silica column chromatography using petroleum ether/ethyl acetate, starting from 10:1 with ethyl acetate gradient.

Example 12—9-Benzyl-2-(piperidin-1-yl)-6-(pyrrolidin-1-yl)-9H-purine

White solid, chemical formula: $C_{21}H_{26}N_6$, yield (%): 68. HPLC-UV/VIS retention time, purity (min., %): 33.38, 99.9. $ESI^{3O}$-MS m/z (rel. int. %, ion): 363.7 (100, $[M+H]^+$). EA (% C, % H, % N, calc./found): 69.58/69.42, 7.23/7.15, 23.19/23.41. $^1$H-NMR (500 MHz, DMSO-$d_6$) δ (ppm): 1.44-1.49 (m, 4H), 1.54-1.57 (m, 2H), 1.89 (bs, 4H), 3.54 (bs, 2H), 3.67-3.69 (m, 4H), 3.95 (bs, 2H), 5.19 (s, 2H), 7.27-7.23 (m, 1H), 7.31 (d, J=4.3 Hz, 4H), 7.81 (s, 1H). $^{13}$C-NMR (125 MHz, DMSO-$d_6$) δ (ppm): 23.6, 24.6, 25.3 (2×C), 25.9, 44.9 (2×C), 45.6, 46.6, 48.1, 113.3, 127.5, 127.7 (2×C), 128.5 (2×C), 137.1, 137.7, 152.3, 152.5, 158.3.

Example 13—9-Benzyl-6-(piperidin-1-yl)-2-(pyrrolidin-1-yl)-9H-purine

White solid, chemical formula: $C_{21}H_{26}N_6$, yield (%): 74. HPLC-UV/VIS retention time, purity (min., %): 33.53, 99.9. $ESI^+$-MS m/z (rel. int. %, ion): 363.7 (100, $[M+H]^+$). EA (% C, % H, % N, calc./found): 69.58/69.49, 7.23/7.51, 23.19/23.02. $^1$H-NMR (500 MHz, DMSO-$d_6$) δ (ppm): 1.49-1.54 (m, 4H), 1.60-1.62 (m, 2H), 1.85-1.87 (m, 4H), 3.44 (t, J=6.6 Hz, 4H), 4.09 (bs, 3H), 5.18 (s, 2H), 7.23-7.27 (m, 1H), 7.30-7.33 (m, 2H), 7.34-7.35 (m, 2H), 7.82 (s, 1H). $^{13}$C-NMR (125 MHz, DMSO-$d_6$) δ (ppm): 24.4, 25.1 (2×C), 25.6 (2×C), 45.4 (2×C), 45.6, 46.4 (2×C), 112.7, 127.6, 127.9 (2×C), 128.5 (2×C), 136.1, 137.6, 152.9, 153.2, 156.9.

Example 14—9-(2,6-Dichlorobenzyl)-2-morpholino-6-(pyrrolidin-1-yl)-9H-purine White solid, chemical formula: $C_{20}H_{22}Cl_2N_6O$, yield (%): 62. HPLC-UV/VIS retention time, purity (min., %): 31.17, 98.1. $ESI^{3O}$-MS m/z (rel. int. %, ion): 433.7 (98, $[^{35}Cl\text{-}M+H]^+$), 435.7 (100, $[^{37}Cl\text{-}M+H]^+$). EA (% C, % H, % N, calc./found): 55.43/55.59, 5.12/5.26, 19.39/19.66. $^1$H-NMR (500 MHz,) δ (ppm): 1.96 (bs, 4H), 3.68 (bs, 2H), 3.76-3.80 (m, 8H), 4.07 (bs, 2H), 5.48 (s, 2H), 7.24 (t, J=8.1 Hz, 1H), 7.35-7.37 (m, 3H). $^{13}$C-NMR (125 MHz, CDCl$_3$) δ (ppm): 24.0, 26.3, 42.4, 45.2 (2×C), 47.2, 48.3, 67.0 (2×C), 113.7, 128.6 (2×C), 130.4, 131.3, 135.9, 136.8 (2×C), 152.2, 152.8, 158.9.

Example 15—9-(2,6-Dichlorobenzyl)-6-morpholino-2-thiomorpholino-9H-purine

White solid, chemical formula: $C_{20}H_{22}Cl_2N_6OS$, yield (%): 58. HPLC-UV/VIS retention time, purity (min., %): 32.77, 99.8. $ESI^{3O}$-MS m/z (rd. int. %, ion): 465.8 (100, $[^{35}Cl\text{-}M+H]^+$), 467.8 (85, $[^{37}Cl\text{-}M+H]^+$). EA (% C, % H, % N, calc./found): 51.61/51.75, 4.76/4.82, 18.06/18.21. $^1$H-NMR (500 MHz, CDCl$_3$) δ (ppm): 2.59-2.61 (m, 4H), 3.79-3.81 (m, 4H), 4.11-4.13 (m, 4H), 4.17 (bs, 4H), 5.48 (s, 2H), 7.25 (dd, J=8.6, 7.3 Hz, 1H), 7.36 (d, J=7.9 Hz, 2H), 7.40 (s, 1H). $^{13}$C-NMR (125 MHz, CDCl$_3$) δ (ppm): 26.5 (2×C), 42.7, 45.2 (2×C), 47.1 (2×C), 66.9 (2×C), 113.5, 128.6 (2×C), 130.4, 131.1, 136.0, 136.7 (2×C), 153.3, 153.8, 157.6.

TABLE 2

Examples of prepared C2,C6-asymmetric 9-(benzylated)-9H-purine derivatives

| | PURINE SUBSTITUENT | | | CHN ANALYSIS [% C, % H, % N] | MS ANALYSIS |
|---|---|---|---|---|---|
| No | C2 | C6 | N9 | [calc/found] | $[M + H]^+$ |
| 77 | piperidin-1-yl | pyrrolidin-1-yl | benzyl | 69.58/69.52, 7.23/7.27, 23.19/23.22 | 363 |
| 78 | pyrrolidin-1-yl | piperidin-1-yl | benzyl | 69.58/69.63, 7.23/7.21, 23.19/23.16 | 363 |
| 79 | morpholin-4-yl | piperidin-1-yl | benzyl | 66.64/66.84, 6.92/6.81, 22.21/22.40 | 379 |
| 80 | piperidin-1-yl | morpholin-4-yl | benzyl | 66.64/66.81, 6.92/7.25, 22.21/22.09 | 379 |
| 81 | pyrrolidin-1-yl | morpholin-4-yl | benzyl | 65.91/65.87, 6.64/6.98, 23.06/22.86 | 365 |
| 82 | piperazin-1-yl | azetidin-1-yl | 2-methylbenzyl | 66.09/65.84, 6.93/7.13, 26.98/27.04 | 363 |
| 83 | morpholin-4-yl | pyrrolidin-1-yl | 2-methylbenzyl | 66.64/66.48, 6.92/7.09, 22.21/22.51 | 378 |
| 84 | piperidin-1-yl | 4-methylpiperazin-1-yl | 3-methylbenzyl | 68.12/68.03, 7.70/7.81, 24.18/24.16 | 405 |
| 85 | azepan-1-yl | pyrrolidin-1-yl | 3-methylbenzyl | 70.74/70.68, 7.74/7.92, 21.52/21.41 | 390 |

TABLE 2-continued

Examples of prepared C2,C6-asymmetric 9-(benzylated)-9H-purine derivatives

| No | PURINE SUBSTITUENT | | | CHN ANALYSIS [% C, % H, % N] [calc/found] | MS ANALYSIS [M + H]+ |
|---|---|---|---|---|---|
| | C2 | C6 | N9 | | |
| 86 | piperazin-1-yl | thiomorpholin-4-yl | 4-methylbenzyl | 61.59/61.74, 6.64/6.49, 23.94/24.06 | 409 |
| 87 | azetidin-1-yl | piperidin-1-yl | 4-methylbenzyl | 69.58/69.35, 7.23/7.44, 23.19/23.21 | 362 |
| 88 | morpholin-4-yl | 4-methylpiperazin-1-yl | 2-hydroxybenzyl | 61.60/61.72, 6.65/6.36, 23.94/24.12 | 409 |
| 89 | azetidin-1-yl | pyrrolidin-1-yl | 2-hydroxybenzyl | 65.12/65.00, 6.33/6.17, 23.98/24.28 | 350 |
| 90 | 4-methylpiperazin-1-yl | piperidin-1-yl | 3-hydroxybenzyl | 64.84/64.59, 7.17/7.36, 24.06/23.81 | 407 |
| 91 | azepan-1-yl | azetidin-1-yl | 3-hydroxybenzyl | 66.64/66.27, 6.92/7.09, 22.21/22.48 | 378 |
| 92 | piperazin-1-yl | morpholin-4-yl | 3-hydroxybenzyl | 60.74/60.61, 6.37/6.45, 24.79/24.54 | 395 |
| 93 | pyrrolidin-1-yl | azepan-1-yl | 4-hydroxybenzyl | 67.32/67.41, 7.19/7.26, 21.41/21.38 | 392 |
| 94 | thiomorpholin-4-yl | piperazin-1-yl | 4-hydroxybenzyl | 58.37/58.42, 6.12/5.97, 23.83/24.00 | 411 |
| 95 | piperidin-1-yl | 4-methylpiperazin-1-yl | 2-methoxybenzyl | 65.53/65.27, 7.41/7.35, 23.26/23.59 | 421 |
| 96 | azetidin-1-yl | thiomorpholin-4-yl | 2-methoxybenzyl | 60.58/50.73, 6.10/6.04, 21.20/21.39 | 396 |
| 97 | morpholin-4-yl | pyrrolidin-1-yl | 2-methoxybenzyl | 63.94/64.06, 6.64/6.78, 21.30/21.42 | 394 |
| 98 | 4-methylpiperazin-1-yl | azepan-1-yl | 3-methoxybenzyl | 66.18/65.81, 7.64/7.49, 22.51/22.36 | 435 |
| 99 | pyrrolidin-1-yl | piperidin-1-yl | 3-methoxybenzyl | 67.32/67.41, 7.19/7.02, 21.41/21.56 | 392 |
| 100 | piperazin-1-yl | 4-methylpiperazin-1-yl | 4-methoxybenzyl | 62.54/62.67, 7.16/7.28, 26.52/26.34 | 422 |
| 101 | thiomorpholin-4-yl | azetidin-1-yl | 4-methoxybenzyl | 60.58/60.64, 6.10/6.22, 21.20/21.09 | 396 |
| 102 | azepan-1-yl | pyrrolidin-1-yl | 2-chlorobenzyl | 64.30/64.32, 6.62/6.70, 20.45/20.34 | 410 |
| 103 | 4-methylpiperazin-1-yl | thiomorpholin-4-yl | 2-chlorobenzyl | 56.81/57.21, 5.90/5.63, 22.08/22.17 | 443 |
| 104 | azetidin-1-yl | piperazin-1-yl | 3-chlorobenzyl | 59.45/59.32, 5.78/5.91, 25.54/25.49 | 383 |
| 105 | pyrrolidin-1-yl | piperidin-1-yl | 4-chlorobenzyl | 63.55/63.36, 6.35/6.52, 21.17/21.19 | 396 |
| 106 | morpholin-4-yl | azepan-1-yl | 4-chlorobenzyl | 61.89/62.16, 6.37/6.03, 19.68/19.91 | 426 |
| 107 | thiomorpholin-4-yl | 4-methylpiperazin-1-yl | 4-chlorobenzyl | 56.81/56.92, 5.90/6.00, 22.08/22.28 | 443 |
| 108 | piperidin-1-yl | morpholin-4-yl | 2-bromobenzyl | 55.15/5.18, 5.51/5.49, 18.37/18.42 | 457 |
| 109 | piperazin-1-yl | azepan-1-yl | 3-bromobenzyl | 56.17/56.28, 6.00/5.84, 20.84/20.96 | 470 |

TABLE 2-continued

Examples of prepared C2,C6-asymmetric 9-(benzylated)-9H-purine derivatives

| No | PURINE SUBSTITUENT C2 | C6 | N9 | CHN ANALYSIS [% C, % H, % N] [calc/found] | MS ANALYSIS [M + H]+ |
|---|---|---|---|---|---|
| 110 | 4-methylpiperazin-1-yl | pyrrolidin-1-yl | 3-bromobenzyl | 55.27/55.36, 5.74/5.37, 21.48/21.55 | 456 |
| 111 | morpholin-4-yl | azetidin-1-yl | 3-bromobenzyl | 53.16/53.00, 4.93/5.13, 19.58/19.61 | 429 |
| 112 | piperidin-1-yl | 4-methylpiperazin-1-yl | 4-bromobenzyl | 56.17/56.29, 6.00/6.35, 20.84/20.71 | 470 |
| 113 | azepan-1-yl | piperidin-1-yl | 4-bromobenzyl | 58.85/59.07, 6.23/6.03, 17.90/17.69 | 469 |
| 114 | piperazin-1-yl | azetidin-1-yl | 2-fluorobenzyl | 53.28/53.29, 5.18/5.23, 22.89/22.91 | 428 |
| 115 | azetidin-1-yl | morpholin-4-yl | 3-fluorobenzyl | 61.94/62.06, 5.75/5.68, 22.81/22.73 | 368 |
| 116 | 4-methylpiperazin-1-yl | azepan-1-yl | 4-fluorobenzyl | 65.22/65.06, 7.14/7.11, 23.15/23.31 | 423 |
| 117 | piperidin-1-yl | pyrrolidin-1-yl | 4-fluorobenzyl | 66.29/66.45, 6.62/6.45, 22.09/22.18 | 380 |
| 118 | pyrrolidin-1-yl | 4-methylpiperazin-1-yl | 2,6-dichlorobenzyl | 56.50/56.62, 5.65/5.41, 21.97/22.19 | 446 |
| 119 | thiomorpholin-4-yl | piperazin-1-yl | 2,6-dichlorobenzyl | 51.72/51.39, 4.99/5.11, 21.11/22.38 | 464 |
| 120 | azetidin-1-yl | pyrrolidin-1-yl | 2,6-dichlorobenzyl | 56.58/56.52, 5.00/5.07, 20.84/20.79 | 403 |

Example 16—Viability Tests on Human Neuroblastoma Cell Line SH-SY5Y (Differentiated Phenotype)

The SH-SY5Y human neuroblastoma cell line obtained as kind gift from Walter d'Acunto (originally purchased from ATCC—American Type Culture Collection (Manassas, VA, USA) was cultivated in Dulbecco's modified Eagle's Medium and Ham's F12 Nutrient Mixture (DMEM:F-12, 1:1), supplemented with 10% fetal bovine serum (FBS) and 1% penicillin and streptomycin at 37° C. in a humidified atmosphere 5% $CO_2$, 95% air in passage limit up to ATCC+ 15. The assay was performed in 96-well microplate with 7000 SH-SY5Y cells per well. Next day, SH-SY5Y underwent all-trans retinoic acid (ATRA)-differentiation for 48 h (ATRA 10 μM). After 48 h, old DMEM/F12 media was removed by fresh media containing tested compounds at 0.1, 1 and 10 μM concentrations for 24 h. The tested compounds were dissolved in DMSO were added into the medium. The maximum concentration of DMSO in media was kept below 0.1% (v/v). The cell viability was measured by Calcein AM (1 mg/ml ThermoFisher) viability assay. Solution of Calcein AM in PBS (0.5 uM) was pipetted to cells and incubated for 50 minutes. After that the fluorescence was measured at 488/517 nm (excitation/emission) using microplate reader Infinite M200 (TECAN). Calcein AM assay is based on the dye-intracellular-esterase cleavage of non-fluorescent dye (Calcein AM) by living cells to fluorescent dye (Calcein), while dyeing cells that lose such ability. The values in Table 4 show % of viability, relative to control of all tested compounds. The control (medium with DMSO, <0.1% (v/v)) was postulated as 100% viability (see the first line of the table). As shown in table 4, all derivatives demonstrated strong stimulating effect on neuronal SH-SY5Y cells.

TABLE 4

The effect of new derivatives on viability of human neuroblastoma cell line SH-SY5Y (differentiated phenotype)

| DMSO ctrl | average | 100.00 | ±SEM | 0.84 | | |
|---|---|---|---|---|---|---|
| Compound | 0.1 μM | ±SEM | 1 μM | ±SEM | 10 μM | ±SEM |
| 1 | 104.80 | 2.09 | 114.03 | 4.68 | 145.94 | 3.04 |
| 4 | 106.29 | 2.13 | 112.63 | 3.49 | 146.44 | 7.06 |
| 5 | 105.87 | 1.76 | 125.72 | 2.53 | 128.71 | 5.16 |
| 26 | 108.14 | 6.34 | 119.64 | 5.70 | 142.50 | 4.46 |
| 30 | 99.49 | 3.12 | 110.63 | 3.24 | 122.84 | 2.87 |
| 35 | 104.22 | 1.86 | 118.77 | 2.36 | 135.02 | 5.53 |
| 42 | 112.01 | 3.06 | 127.94 | 3.61 | 138.52 | 2.95 |
| 74 | 111.48 | 3.05 | 138.17 | 2.85 | 151.69 | 2.93 |
| 77 | 107.19 | 4.63 | 118.15 | 3.90 | 116.98 | 3.96 |
| 78 | 105.72 | 2.48 | 120.35 | 5.02 | 134.18 | 2.62 |

Example 17—Viability Test on Human Neuroblastoma Cell Line SH-SY5Y (Differentiated Phenotype)—Salsolinol-Induced Model of Parkinson's Disease (PD)

Similarly, to the previous test the assay was performed in 96-well microplates with 7000 SH-SY5Y cells per well. Day after the seeding of cells, SH-SY5Y underwent all-trans retinoic acid (ATRA)-differentiation for 48 h (ATRA 10 µM). After 48 h, old DMEM/F12 media was removed by fresh media containing 500 µM dopaminergic neurotoxin Salsolinol (SAL) without or with tested compounds at 0.1, 1 and 10 µM concentrations. Deferoxamine (DFO), Donepezil (DON), and ZM241385 (ZM) were chosen as positive controls and for stratification of activity of tested compounds. After 24 h the cell viability was measured by Calcein AM viability assay. Salsolinol induced a significant decrease in percentages of alive cells accounting for 30.7%. All tested examples demonstrated strong and even higher protective effect than standard drugs such as DFO, ZM and DON. Compounds 30 and 1 showed the highest and superior protective effect (26.41% and 26.08%) to positive controls at 10 µM. Interestingly compound 74 demonstrated strong neuroprotection starting at 1 µM to 10 µM (20.24% and 22.35%). Overall, all compounds demonstrated highly potent and superior neuroprotective effect at 10 µM than positive controls DFO, ZM and DON see FIG. 1 and Table 5.

TABLE 5

Neuroprotective effects of novel compounds on human neuroblastoma cell line SH-SY5Y (differentiated phenotype)

| Compound | Neuroprotective effect (% of control) | | | p value |
|---|---|---|---|---|
| | 0.1 µM | 1 µM | 10 µM | |
| ZM241385 (ZM) | 1.95 | 7.03 | 9.31 | >0.001 |
| Defferoxamine (DFO) | 1.43 | 4.86 | 10.52 | >0.001 |
| Donepezil (DON) | 2.76 | 6.73 | 14.25 | >0.001 |
| 1 | N/A | 3.03 | 26.08 | >0.001 |
| 4 | 1.70 | 8.11 | 21.12 | >0.001 |
| 5 | 7.03 | 18.72 | 19.89 | >0.001 |
| 26 | 4.90 | 14.43 | 20.71 | >0.001 |
| 30 | 10.62 | 16.04 | 26.41 | >0.001 |
| 35 | 1.19 | 13.01 | 19.11 | >0.001 |
| 42 | 6.86 | 15.44 | 20.05 | >0.001 |
| 74 | 8.57 | 20.24 | 22.35 | >0.001 |
| 77 | 4.64 | 12.11 | 13.8 | >0.001 |
| 78 | N/A | 17.95 | N/A | >0.001 |

N/A = no protection

Example 18—Measurement of Oxidative Stress on Human Neuroblastoma Cell Line SH-SY5Y—Salsolinol-Induced Model of PD The assay was performed in 96-well microplate with 7000 cells/well. Next day, SH-SY5Y underwent differentiation protocol for 48 h see above. Treatment procedure remained the same as in previous section (Cell treatment and viability/cytotoxicity assays). Additionally, oxidative stress (OS) inducers such as 6-hydroxydopamine (6-OHDA) and glutamate (Glu) alone were used as negative controls. Negative controls determined threshold of excessive OS. After 6 h of incubation of cells with medium with toxin alone (SAL 500 µM), the combination of toxin and the tested compounds (SAL 500 µM and compounds in active concentrations: 1 and 10 µM), DMSO control and negative controls (6-OHDA and Glu), the medium was replaced by PBS containing 10 µM dihydroethidium (DHE) and then shaken for 30 minutes. After 30 minutes, DHE was read at 500 nm/580 nm (excitation/emission). DHE is cell permeable dye which is selective toward superoxide radical detection. The control (medium with DMSO, <0.1% (v/v)) was postulated as 100% OS, while in the group of Salsolinol (toxin) tripled the level of OS, accounting for 335.4%. Compounds showed OS decreasing activity. Among all derivatives, compounds 30 and 5 showed highest potency toward the reduction of oxidative stress (OS) induced by endogenous neurotoxin Salsolinol. On the other hand, compound 78 at 10 µM demonstrated OS level reaching threshold of negative controls 6-hydroxydopamine and Glutamate, which expected due to the decreased of viability after 24 h in Salsolinol-induced model of PD, see FIG. 1. Overall, lead compounds 30 and 5 showed slightly better or equal OS reduction activity reduction activity as best positive control Donepezil, but their general neuroprotective activity surpassed Donepezil even at 1 µM concentration. Shifting of therapeutic window (neuroprotective activity and reduction of ROS) into lower concentrations e.g. compounds 30 and 5 vs Donepezil is beneficial for the design of new potential drug.

TABLE 6

Oxidative stress-induced by endogenous neurotoxin Salsolinol and ROS reduction activity of novel compounds when tested on the human neuroblastoma cell line SH-SY5Y

| Compound | Oxidative stress (% of control) | |
|---|---|---|
| | average | SEM± |
| DMSO control | 99.60 | 2.08 |
| Salsolinol 500 µM | 335.36 | 21.61 |
| 6-OHDA 30 µM$^\Delta$ | 215.43 | 21.97 |
| Glu 160 mM$^\Delta$ | 268.62 | 19.07 |
| Positive controls | 10 µM | SEM± |
| ZM241385 | 102.30 | 12.47 |
| Deferoxamine (DFO) | 100.95 | 6.83 |
| Donepezil (DON) | 120.10 | 11.71 |

| Examples | 1 µM | SEM± | 10 µM | SEM± |
|---|---|---|---|---|
| 1* | 124.48 | 9.55 | 157.22 | 5.21 |
| 4* | 105.57 | 7.17 | 155.38 | 22.62 |
| 5* | 121.19 | 6.18 | 135.37 | 10.80 |
| 26* | 107.47 | 8.56 | 142.22 | 17.81 |
| 30* | 95.86 | 7.53 | 97.44 | 5.50 |
| 35* | 161.97 | 24.87 | 214.57 | 42.74 |
| 42* | 171.55 | 29.23 | 173.94 | 23.60 |
| 74* | 125.98 | 10.74 | 178.95 | 20.35 |

TABLE 6-continued

Oxidative stress-induced by endogenous neurotoxin Salsolinol and ROS reduction activity of novel compounds when tested on the human neuroblastoma cell line SH-SY5Y

| 77* | 118.21 | 10.14 | 126.84 | 8.33 |
| 78* | 135.70 | 9.58 | 238.45 | 20.11 |

*Mean (n = 9), ᐃnegative controls

Example 19—Radical Scavenging Activity Determined by ORAC Assay

The ability of compounds to scavenge free radicals in vitro was determined by Oxygen Radical Absorbance Capacity (ORAC) method. In brief, fluorescein (100 μL, 500 mM) and 25 μL of tested compound solution were added into each working well in a 96-well microplate preincubated at 37° C. Thereafter, 25 μL of 250 mM 2,2'-azobis(2-amidino-propan)dihydrochloride (AAPH) was quickly added, microplate was shaken for 5 s and the fluorescence (Ex. 485 nm, Em. 510 nm) was read every 3 min over 90 min by using microplate reader Infinite 200 (TECAN, Switzerland). The NAUC value (Net Area Under Curve) was used to express antioxidant activity relative to trolox (hydrophilic equivalent of vitamin E postulated as a standard). Substances with an ORAC value greater than 0 actively trap free radicals.

| Compound | ORAC (compound/trolox) |
|---|---|
| 1 | 0.052 ± 0.002 |
| 4 | 0.007 ± 0.002 |
| 5 | 0.016 ± 0.001 |
| 26 | 0.126 ± 0.018 |
| 30 | 0.422 ± 0.034 |
| 35 | 0.033 ± 0.001 |
| 42 | 0.029 ± 0.002 |
| 74 | 0.029 ± 0.004 |
| 77 | 0.028 ± 0.001 |
| 78 | 0.071 ± 0.005 |

*Mean ± SD (n = 3)

Example 20—Activation of Transcription Factor Nrf2

The ability of compounds to activate Nrf2-dependent expression was determined by EpRE-LUX reporter cell line. In brief, compounds at 100, 10, 1 and 0.1 μM concentrations of the tested compounds were incubated for 24 h with the cells. After cells lysis (10 mM Tris, 2 mM DTT), a buffer containing 0.2 mM luciferin was added to start luminescent reaction. The increase in luminescence was measured with microplate reader Infinite M200 (TECAN). Compounds with Nrf2 value higher than 0 are strong Nrf2 activators and thus will be useful agents for the treatment of neurodegenerative diseases associated with oxidative stress.

| Compound | Nrf2 (relative luminiscence) |
|---|---|
| 1 | 0.27 ± 0.06 |
| 4 | 0.19 ± 0.02 |
| 5 | 0.17 ± 0.06 |
| 26 | 0.33 ± 0.06 |
| 30 | 0.29 ± 0.11 |
| 35 | 0.04 ± 0.00 |
| 42 | 0.00 ± 0.00 |
| 74 | 0.38 ± 0.08 |
| 77 | 0.16 ± 0.04 |
| 78 | 0.23 ± 0.03 |

*Mean ± SD (n = 3)

Example 21—Formulations

The growth regulatory formulations usually contain from 0.1 to 99% by weight, especially from 0.1 to 95% by weight, of active ingredient mixture comprising a C2,C6-disubstituted-9-benzylated-9H-purine derivative of this invention, from 1 to 99.9% by weight of a solid or liquid formulation adjuvant, and from 0 to 25% by weight, especially from 0.1 to 25% by weight, of a surfactant. Whereas commercial products are usually formulated as concentrates, the end user will normally employ dilute formulations. The compositions may also comprise further ingredients, such as stabilizers, e.g., vegetable oils or epoxidized vegetable oils (epoxidized coconut, rapeseed oil or soybean oil), antifoams, e.g., silicone oil, preservatives, viscosity regulators, binders, tackifiers, and also fertilisers or other active ingredients. Preferred formulations have especially the following compositions: (%=percent by weight):

| F1. Wettable powders | a) | b) | c) | d) |
|---|---|---|---|---|
| active ingredient mixture | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly dispersed silicic acid | 1% | 3% | 5% | 10% |
| kaolin | 88% | 62% | 35% | — |

The active ingredient is mixed thoroughly with the adjuvants and the mixture is thoroughly ground in a suitable mill, affording wettable powders which can be diluted with water to give suspensions of any desired concentration.

| F2. Suspension concentrates | a) | b) | c) | d) |
|---|---|---|---|---|
| active ingredient mixture | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjutants, giving a suspension concentrate from which suspensions of any desired concentration can be obtained by dilution with water.

F3. Dry Capsules 5000 capsules, each of which contain 0.25 g of one of the C2,C6-disubstituted-9-benzyl-9H-purine derivative as active ingredient, are prepared as follows:

Composition: Active ingredient: 1250 g; Talc: 180 g; Wheat starch: 120 g; Magnesium stearate: 80 g; Lactose 20 g.

Preparation process: The powdered substances mentioned are pressed through a sieve of mesh width 0.6 mm Portions of 0.33 g of the mixture are transferred to gelatine capsules with the aid of a capsule-filling machine.

F4. Soft Capsules 5000 soft gelatine capsules, each of which contain 0.05 g of one of the C2,C6-disubstituted-9-benzyl-9H-purine derivative as active ingredient, are prepared as follows:

Composition: 250 g Active ingredient +2 litres Lauroglycol

Preparation process: The powdered active ingredient is suspended in Lauroglykol® (propylene glycol laurate, Gattefossé S.A., Saint Priest, France) and ground in a wet-pulveriser to a particle size of about 1 to 3 mm Portions of in each case 0.419 g of the mixture are then transferred to soft gelatine capsules by means of a capsule-filling machine.

F5. Soft Capsules 5000 soft gelatine capsules, each of which contain 0.05 g of one of the C2,C6-disubstituted-9-benzyl-9H-purine derivative as active ingredient, are prepared as follows:

Composition: 250 g Active ingredient +1 litre PEG 400 +1 litre Tween 80

Preparation process: The powdered active ingredient is suspended in PEG 400 (polyethylene glycol of Mr between 380 and about 420, Sigma, Fluka, Aldrich, USA) and Tween® 80 (polyoxyethylene sorbitan monolaurate, Atlas Chem. Inc., Inc., USA, supplied by Sigma, Fluka, Aldrich, USA) and ground in a wet-pulveriser to a particle size of about 1 to 3 mm Portions of in each case 0.43 g of the mixture are then transferred to soft gelatine capsules by means of a capsule-filling machine.

Example 22—Formulation of Tablets with Controlled Release

One tablet contains, for example, 300-350 mg of C2, C6-disubstituted-9-benzyl-9H-purine as active ingredient.

Excipient with known effect: Each tablet contains 150 to 200 mg of a retardant (Methocel, Parteck® SRP 80, Kollidon® SR, Kollidon 25, chitosan, alginate), as well as a lubricant (magnesium stearate), active substances (VH), binders (Prosolv SMCC 90).

The dosage form is a controlled release tablet.

Tablet preparation: Tablets are prepared by direct compression. First, the calculated amount of retarding component (Methocel, Parteck® SRP 80, Kollidon® SR, Kollidon 25, chitosan, alginate), weighing agent (magnesium stearate), active ingredient (VH), binder (Prosolv SMCC 90) are weighed. The resulting mixture is then homogenized in a homogenizer (Retsch MM200—Retsch GmbH, Haan). It is recommended to carry out the homogenization at three frequencies: 10 oscillations/s, 13 and 15 oscillations/s for 1 minute each. The tablet is then transferred to a hand press. The tablets are compressed at a load of 8 kN for 5 minutes.

The load is selected with respect to the desired tablet strength of 0.8 to 0.8 MPa. The tablet weight is 500±5 mg.

Hydrophilic Matrix Tablets with Hypromellose

The tablets are prepared by the direct compression method as described above.

The tablet weight was 500±5 mg. Composition of hydrophilic tablets with hypromellose in wt. %:

| Formulation | A1 | A2 | A3 |
| --- | --- | --- | --- |
| Prosolv SMCC 90 | 49 | 49 | 49 |
| Methocel K4M | 0 | 30 | 0 |
| Methocel K15M | 30 | 0 | 0 |
| Methocel K100M | 0 | 0 | 30 |
| Active substance | 20 | 20 | 20 |
| Magnesium stearate | 1 | 1 | 1 |

Hydrophilic Matrix Tablets with Retarding Component Kollidon 25, Kollidon® SR, Parteck® SRP 80

The tablets are prepared by the direct compression method as described above.

The tablet weight was 500±5 mg. Composition of hydrophilic tablets in wt. %:

| Formulation | F1 | F2 | F3 | F4 | F5 |
| --- | --- | --- | --- | --- | --- |
| Prosolv ® SMCC 90 | 49 | 49 | 49 | 49 | 49 |
| Kollidon 25 | 30 | 20 | 10 | 0 | 0 |
| Kollidon ® SR | 0 | 0 | 0 | 30 | 0 |
| Parteck ® SRP 80 | 0 | 0 | 0 | 0 | 30 |
| Active substance | 20 | 30 | 40 | 20 | 20 |
| Magnesium stearate | 1 | 1 | 1 | 1 | 1 |

Hydrophilic matrix tablets containing LubriTose™ MCC, Methocel KJ5M Nebo Methocel K4M The tablets are prepared by the direct compression method as described above.

The tablet weight was 500±5 mg. Composition of hydrophilic tablets in wt. %:

| Formulation | F1 | F2 |
| --- | --- | --- |
| LubriTose ™ MCC | 50 | 50 |
| Methocel K15M | 30 | 0 |
| Methocel K4M | 0 | 30 |
| Active substance | 20 | 20 |

The invention claimed is:

1. Heterocyclic nitrogen-containing purine derivative of the general formula I,

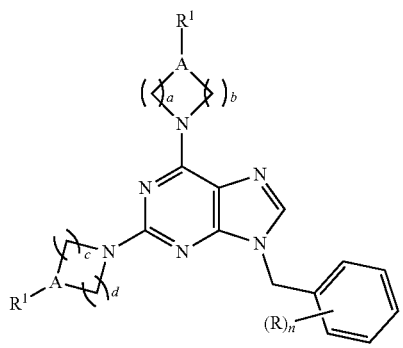

wherein
R are independently selected from the group consisting of H, Cl, Br, methyl, OH, and methoxy, and n=1 or 2;

$R^1$ is independently on each occurrence H or methyl, or $R^1$ is not present;

A is independently on each occurrence selected from the group consisting of C, N S;

a, b, c, d are, independently of each other, an integer selected from 1, 2, 3;

provided that the compound of formula I is not 2,6-dimorpholino-9-benzylpurine;

and the pharmaceutically acceptable salts thereof.

2. The heterocyclic nitrogen-containing purine derivative according to claim 1 which bears a substituent —[N—$(CH_2)_c$ -$A(R^1)$—$(CH_2)_d$-] in position 2, selected from the group consisting of azetidin-1-yl, pyrrolidin-1-yl, piperidin-1-yl, thiomorpholino, piperazin-1-yl, 4-methylpiperazin-1-yl, azepan-1-yl, azocan-1-yl, and 1,5-thiazocan-5-yl.

3. The heterocyclic nitrogen-containing purine derivative according to claim 1 which bears a substituent —[N—$(CH_2)_a$ -$A(R^1)$—$(CH_2)_b$-] in position 6, selected from the group consisting of azetidin-1-yl, pyrrolidin-1-yl, piperidin-1-yl, thiomorpholino, piperazin-1-yl, 4-methylpiperazin-1-yl, azepan-1-yl, azocan-1-yl, and 1,5-thiazocan-1-yl.

4. The heterocyclic nitrogen-containing purine derivative according to claim 1 which bears a substituent —$CH_2$—$C_6H_4(R)_n$ in position 9, which is selected from the group consisting of benzyl, 2-chlorobenzyl, 3-chlorobenzyl, 4-chlorobenzyl, 2,6-dichlorobenzyl, 2-bromobenzyl, 3-bromobenzyl, 4-bromobenzyl, 2-methylbenzyl, 3-methylbenzyl, 4-methylbenzyl, 2-hydroxybenzyl, 3-hydroxybenzyl, 4-hydroxybenzyl, 2-methoxybenzyl, 3-methoxybenzyl, and 4-methoxybenzyl.

5. The heterocyclic nitrogen-containing purine derivative according to claim 1, selected from the group consisting of 2,6-di(azetidin-1-yl)-9-(3-hydroxybenzyl)-9H-purine, 2,6-di(azetidin-1-yl)-9-(4-hydroxybenzyl)-9H-purine, 9-(4-hydroxybenzyl)-2,6-di(pyrrolidin-1-yl)-9H-purine, 9-benzyl-2-(piperidin-1-yl)-6-(pyrrolidin-1-yl)-9H-purine, 9-benzyl-6-(piperidin-1-yl)-2-(pyrrolidin-1-yl)-9H-purine, 9-benzyl-2,6-dithiomorpholino-9H-purine, 9-(4-hydroxybenzyl)-2,6-dithiomorpholino-9H-purine, 2-(azetidin-1-yl)-9-(4-hydroxybenzyl)-6-thiomorpholino-9H-purine, 9-(4-hydroxybenzyl)-2-(pyrrolidin-1-yl)-6-thiomorpholino-9H-purine, and 2,6-di(azepan-1-yl)-9-(4-hydroxybenzyl)-9H-purine.

6. A method of treatment or prophylaxis of a neurodegenerative disease, comprising the step of administering the heterocyclic, nitrogen-containing purine derivative according to claim 1 to a patient in need thereof.

7. The method according to claim 6, wherein the neurodegenerative disease is selected from the group consisting of amyotrophic lateral sclerosis, Parkinson's disease, Alzheimer's disease, Huntington's disease, progressive supranuclear palsy, corticobasal degeneration, frontotemporal dementia, Lewy body dementia, multiple system atrophy, chronic traumatic encephalopathy, and spinocerebellar ataxia.

8. A pharmaceutical composition comprising one or more heterocyclic nitrogen-containing purine derivatives according to claim 1 and at least one pharmaceutically acceptable excipient.

9. The heterocyclic nitrogen-containing purine derivative according to claim 1, wherein the pharmaceutically acceptable salts are selected from salts with alkali metals, ammonium or amines, and addition salts with acids.

\* \* \* \* \*